US008002841B2

(12) United States Patent
Hasselman

(10) Patent No.: US 8,002,841 B2
(45) Date of Patent: Aug. 23, 2011

(54) METHOD OF PREPARING AN ANKLE JOINT FOR REPLACEMENT, JOINT PROSTHESIS, AND CUTTING ALIGNMENT APPARATUS FOR USE IN PERFORMING AN ARTHROPLASTY PROCEDURE

(75) Inventor: Carl T. Hasselman, Oakmont, PA (US)

(73) Assignee: Synthes USA, LLC, West Chester, PA (US)

( * ) Notice: Subject to any disclaimer, the term of this patent is extended or adjusted under 35 U.S.C. 154(b) by 82 days.

(21) Appl. No.: 12/161,244

(22) PCT Filed: Jan. 12, 2007

(86) PCT No.: PCT/US2007/060470
§ 371 (c)(1),
(2), (4) Date: Jul. 17, 2008

(87) PCT Pub. No.: WO2007/084846
PCT Pub. Date: Jul. 26, 2007

(65) Prior Publication Data
US 2008/0306605 A1    Dec. 11, 2008

Related U.S. Application Data

(60) Provisional application No. 60/761,007, filed on Jan. 20, 2006, provisional application No. 60/781,634, filed on Mar. 13, 2006.

(51) Int. Cl.
*A61F 2/42* (2006.01)
(52) U.S. Cl. .................................. 623/21.18
(58) Field of Classification Search ............. 623/21.18, 623/20.14, 20.15, 20.26, 20.27, 20.28, 20.29, 623/20.31, 20.33, 21.11, 21.12, 21.17
See application file for complete search history.

(56) References Cited

U.S. PATENT DOCUMENTS

| | | | | |
|---|---|---|---|---|
| 3,896,502 A | * | 7/1975 | Lennox | 623/21.18 |
| 4,069,518 A | * | 1/1978 | Groth et al. | 623/21.18 |
| 4,755,185 A | * | 7/1988 | Tarr | 623/23.4 |
| 5,609,639 A | * | 3/1997 | Walker | 623/20.29 |
| 5,681,352 A | | 10/1997 | Clancy, III et al. | |
| 5,755,801 A | * | 5/1998 | Walker et al. | 623/20.21 |
| 5,766,259 A | * | 6/1998 | Sammarco | 623/21.18 |

(Continued)

OTHER PUBLICATIONS

Leardini et al., "Mobility of the Ankle and Design of Total Ankle Replacement", Clinical Orthopaedics and Related Research, No. 424, Jul. 2004, pp. 41-42.

(Continued)

*Primary Examiner* — Alvin J. Stewart
(74) *Attorney, Agent, or Firm* — Fay Kaplun & Marcin, LLP

(57) ABSTRACT

A method prepares an ankle joint of a patient for replacement. The patient includes a tibia (20) having a medial portion (22), a talus (40), and an ankle (10) having a medial portion. The method employs a cutting alignment apparatus (50) including a first portion external to the patient and a second portion, and surgically prepares and exposes the medial portion of the ankle for replacement. The second portion of the cutting alignment apparatus is coupled to the tibia, and a cutting guide (90) is disposed with respect to the cutting alignment apparatus. The medial portion of the tibia is detached, a portion of the tibia proximate the talus is cut, and a portion of the talus proximate the tibia is cut. An ankle prosthesis (100) is installed to the ankle, and the medial portion of the tibia is reattached.

10 Claims, 18 Drawing Sheets

U.S. PATENT DOCUMENTS

| | | | | |
|---|---|---|---|---|
| 5,824,106 | A * | 10/1998 | Fournol | 623/21.18 |
| 6,080,195 | A * | 6/2000 | Colleran et al. | 623/20.32 |
| 6,090,144 | A * | 7/2000 | Letot et al. | 623/20.34 |
| 6,162,254 | A * | 12/2000 | Timoteo | 623/20.33 |
| 6,168,631 | B1 | 1/2001 | Maxwell et al. | |
| 6,183,519 | B1 * | 2/2001 | Bonnin et al. | 623/21.18 |
| 6,210,445 | B1 * | 4/2001 | Zawadzki | 623/20.33 |
| 6,217,618 | B1 * | 4/2001 | Hileman | 623/20.33 |
| 6,409,767 | B1 * | 6/2002 | Perice et al. | 623/21.18 |
| 6,413,279 | B1 * | 7/2002 | Metzger et al. | 623/20.29 |
| 6,485,520 | B1 * | 11/2002 | Hubach et al. | 623/21.13 |
| 6,663,669 | B1 | 12/2003 | Reiley | |
| 6,814,757 | B2 * | 11/2004 | Kopylov et al. | 623/21.11 |
| 6,890,358 | B2 * | 5/2005 | Ball et al. | 623/21.13 |
| 6,926,739 | B1 | 8/2005 | O'Connor et al. | |
| 6,939,380 | B2 * | 9/2005 | Guzman | 623/21.18 |
| 6,969,407 | B2 * | 11/2005 | Klotz et al. | 623/21.12 |
| 7,011,687 | B2 * | 3/2006 | Deffenbaugh et al. | 623/21.18 |
| 7,025,790 | B2 * | 4/2006 | Parks et al. | 623/21.18 |
| 7,238,190 | B2 | 7/2007 | Schon et al. | |
| 7,323,012 | B1 * | 1/2008 | Stone et al. | 623/21.18 |
| 7,465,319 | B2 * | 12/2008 | Tornier | 623/19.11 |
| 7,485,147 | B2 * | 2/2009 | Pappas et al. | 623/21.18 |
| 7,534,270 | B2 * | 5/2009 | Ball | 623/21.18 |
| 7,597,713 | B2 * | 10/2009 | Baumgartner et al. | 623/17.15 |
| 7,625,409 | B2 * | 12/2009 | Saltzman et al. | 623/21.18 |
| 7,628,819 | B2 * | 12/2009 | Gupta et al. | 623/21.11 |
| 2001/0014827 | A1 * | 8/2001 | Chambat et al. | 623/20.33 |
| 2003/0181985 | A1 * | 9/2003 | Keller et al. | 623/21.18 |
| 2003/0187511 | A1 * | 10/2003 | Ball et al. | 623/21.13 |
| 2003/0204265 | A1 * | 10/2003 | Short et al. | 623/21.18 |
| 2004/0133282 | A1 * | 7/2004 | Deffenbaugh et al. | 623/21.18 |
| 2004/0167631 | A1 * | 8/2004 | Luchesi et al. | 623/21.18 |
| 2004/0210227 | A1 | 10/2004 | Trail et al. | |
| 2005/0049711 | A1 * | 3/2005 | Ball | 623/21.18 |
| 2005/0182492 | A1 * | 8/2005 | Pappas et al. | 623/21.18 |
| 2005/0192673 | A1 | 9/2005 | Saltzman et al. | |
| 2005/0251137 | A1 | 11/2005 | Ball | |
| 2005/0288792 | A1 | 12/2005 | Landes et al. | |
| 2006/0142870 | A1 | 6/2006 | Robinson et al. | |
| 2006/0229730 | A1 * | 10/2006 | Railey et al. | 623/21.18 |
| 2006/0247788 | A1 * | 11/2006 | Ross | 623/21.18 |
| 2007/0112432 | A1 * | 5/2007 | Reiley | 623/21.18 |
| 2007/0173947 | A1 * | 7/2007 | Ratron et al. | 623/21.18 |
| 2009/0182433 | A1 * | 7/2009 | Reiley et al. | 623/18.11 |
| 2009/0240338 | A1 * | 9/2009 | Reiley | 623/21.18 |

OTHER PUBLICATIONS

Davidson, T., "Arthroplasty Health Article", HealthLine, 2005-2006, 3 pp.

Freedman, K., "Ankle Replacement Health Article", HealthLine, 2005-2006, 3 pp.

* cited by examiner

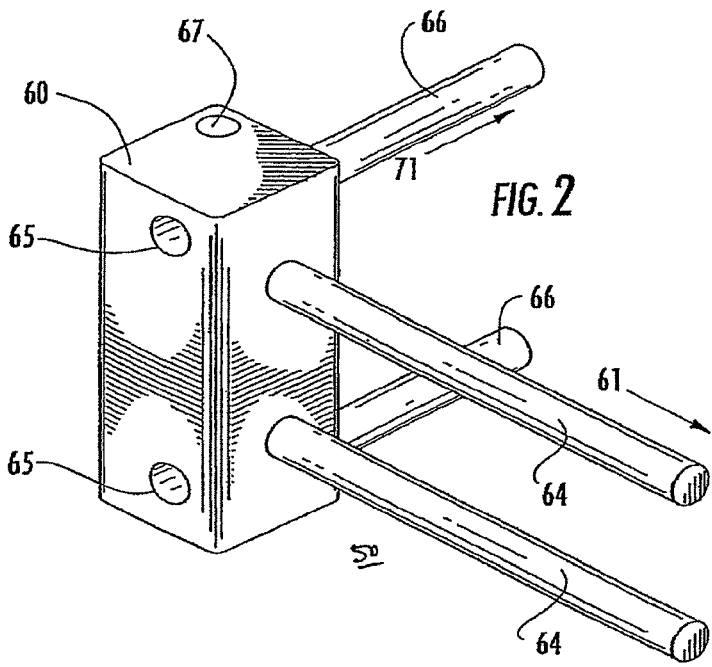
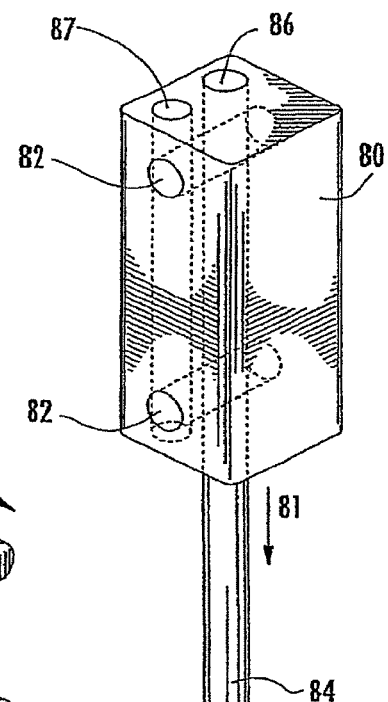
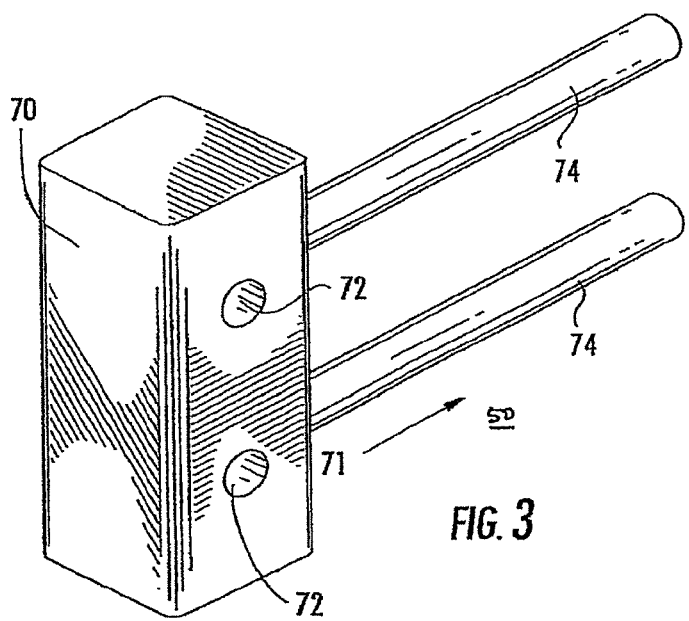
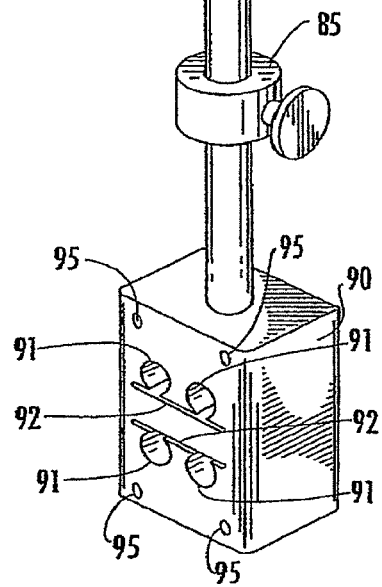

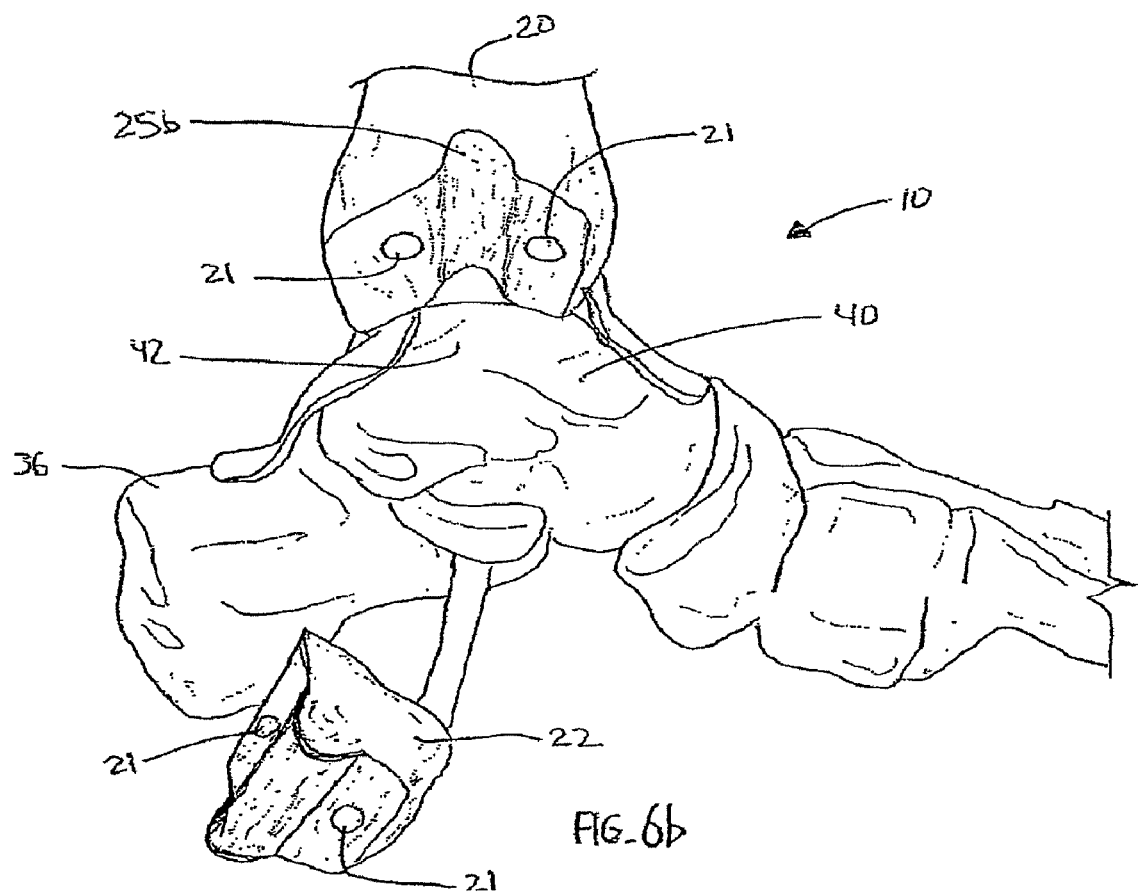

US 8,002,841 B2

METHOD OF PREPARING AN ANKLE JOINT FOR REPLACEMENT, JOINT PROSTHESIS, AND CUTTING ALIGNMENT APPARATUS FOR USE IN PERFORMING AN ARTHROPLASTY PROCEDURE

CROSS-REFERENCE TO RELATED APPLICATIONS

This application claims the benefit of U.S. Provisional Patent Application Ser. No. 60/761,007, filed Jan. 20, 2006; and of U.S. Provisional Patent Application Ser. No. 60/781,634, filed Mar. 13, 2006.

BACKGROUND OF THE INVENTION

1. Field of the Invention

This invention relates to a method of preparing an ankle joint for replacement, and more particularly to an ankle prosthesis and a method of preparing the ankle joint for replacement implementing such ankle prosthesis and an alignment apparatus that enables such replacement to be performed from a medial position on the ankle.

2. Background Information

Ankle prostheses and ankle replacement methods have been implemented for the past few decades producing numerous prostheses and approaches to the treatment of diseased, injured or otherwise compromised ankle joints.

Many types of total ankle prostheses have been developed including a cylindrical-type ankle replacement, the spherical-type ankle replacement, the sliding cylindrical-type ankle replacement, the Buechel-Pappas Total Ankle Replacement System, the Scandinavian Total Ankle Replacement system, or STAR system, Hintegra ankle system, ESKA implant, and the Agility™ Total Ankle System. Generally two broad categories exist in ankle replacement prostheses, fixed-bearing ankle implants having fixed components and mobile-bearing implants having mobile components. The fixed-bearing ankle implants are generally semi-constrained, although some are filly constrained, to have a single articulation capability between a tibial and a talar component with some allowance for rotation. The mobile-bearing implants have minimal constraints due to the articulation permitted by a meniscus positioned between tibial and talar components.

Many ankle prostheses in the United States are the fixed-bearing ankle implant type, such as the Agility™ Total Ankle System, due to its FDA approval status. In these types of semi-constrained fixed bearing devices, the tibial prosthesis component and the talar prosthesis component have a plastic insert slidingly positioned within the tibial component between the two components. In these fixed-bearing ankle implants, the two components generally work directly with each other in various fashions and all require incisions and installation from an anterior position on the ankle, save certain methods published for the ESKA ankle replacement.

Most of the known prostheses further require significant amounts of bone to be resected from the tibia and talus in order to install the traditionally bulky components into the ankle joint. As is well known in the art, the more bone that is removed, or resected, the more likely the failure of the component as the bone typically is its hardest at its outside surface. Thus, many devices fail for reasons of subsidence of the component wherein the significant bone resection and the implanting of a component will cause the component to crush into the cancellous bone over time under pressure.

Another ankle replacement that has been developed is the ESKA implant which differs from the other ankle implants in that it requires incision and installation from a lateral position on the ankle. However, this preparation requires the devascularization of the fibula, release of the syndesmotic ligaments and significant bone resection.

No known prosthesis disclosed is designed, configured and installed from a medial position on the ankle.

Some of the most common problems encountered with prior art ankle prostheses are loosening of the components, instability, loss of bone support, subsidence, inadequate motion and noticeable scaring on the most visible parts of the ankle. Further, and more importantly, ankle replacement is more challenging than other procedures such as hip or knee replacement due to the limited soft tissue envelope that is sparse at the ankle and has minimal flexibility. Thus, ankle replacement is associated with a high complication rate. This complication rate is exacerbated by the dense intersection of tendons and nerves in the anterior (or front) and lateral sides of the ankle.

Accordingly, wound problems are not uncommon due to the present techniques and prostheses known in the art.

SUMMARY OF THE INVENTION

The present invention is directed to a method and apparatus for ankle replacement. A cutting alignment apparatus may be provided for assisting in performing an arthroplasty procedure. The cutting alignment apparatus may include a first positioner having first rods extending therefrom in a first direction and first alignment extensions extending from the first positioner in a second direction. The first positioner may further have securing apertures extending through the first positioner in a second direction. A second positioner may have second rods extending therefrom in the second direction. The second positioner may further have second apertures extending therethrough in the first direction and may be in communication with the first positioner via the first rods, which are positioned within the second apertures. A third positioner may have third apertures extending therethrough in the second direction wherein the third positioner is in communication with the second positioner via the second rods positioned within the third apertures. The third positioner may further have a fourth aperture extending therethrough in a third direction.

The method of ankle replacement may comprise the steps of employing an external fixator apparatus to position an ankle, surgically preparing and exposing a medial portion of the ankle for replacement, forming at least one alignment aperture in a medial portion of the tibia and performing an osteotomy of the medial portion of the tibia, applying a cutting alignment apparatus such that a cutting guide of the cutting alignment apparatus is positioned in a desired orientation, cutting a portion of a tibia and a talus of the ankle, installing an ankle prosthesis and reattaching the medial portion of the tibia.

In accordance with one aspect of the invention, a joint prosthesis comprises: a first joint component having a first locking feature; a second joint component; and a meniscus insert disposed between the first joint component and the second joint component, wherein the meniscus insert has a second locking feature, which is structured to lock to the first locking feature of the first joint component, and wherein the first and second locking features are both structured to permit the meniscus insert to pivot with respect to the first joint component.

As another aspect of the invention, a method prepares an ankle joint of a patient for replacement. The patient includes a tibia having a medial portion, a talus, and an ankle having a medial portion. The method comprises: employing a cutting alignment apparatus including a first portion external to the patient and a second portion; surgically preparing and exposing the medial portion of the ankle for replacement; coupling the second portion of the cutting alignment apparatus to the tibia; disposing a cutting guide with respect to the cutting alignment apparatus; detaching the medial portion of the tibia; cutting a portion of the tibia proximate the talus; and cutting a portion of the talus proximate the tibia.

As another aspect of the invention, a cutting alignment apparatus is for use in performing an arthroplasty procedure of a patient including a tibia having a medial portion, a talus, and an ankle. The cutting alignment apparatus comprises: a first positioner comprising first rods extending therefrom in a first direction and first alignment extensions extending from the first positioner in a second direction, the first positioner being structured to be secured to the tibia; a second positioner comprising second rods extending therefrom in the second direction, and second apertures extending therethrough in the first direction, the first rods of the first positioner being positioned within the second apertures; a third positioner comprising third apertures extending therethrough in the second direction, a fourth aperture extending therethrough in a third direction, and a third rod extending from the fourth aperture, the second rods of the second positioner being positioned within the third apertures; and a cutting guide positioned from the third rod and being structured to face the medial portion of the tibia and the talus.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended to unduly limit the present invention. As used in the specification and the claims, the singular form of "a", "an", and "the" include plural referents unless the context clearly dictates otherwise.

BRIEF DESCRIPTION OF THE DRAWINGS

FIG. 2 shows a perspective view of an embodiment of a first positioner in accordance with the present invention;

FIG. 3 is a perspective view of an embodiment of a second positioner in accordance with the present invention;

FIG. 4 is a perspective view of an embodiment of a third positioner having a cutting guide positioned thereon in accordance with the present invention;

FIG. 6b illustrates a lateral view of an ankle that has undergone an embodiment of a preparation step for the medial portion of the tibia in accordance with the present invention;

DESCRIPTION OF THE PREFERRED EMBODIMENTS

Figure 1:
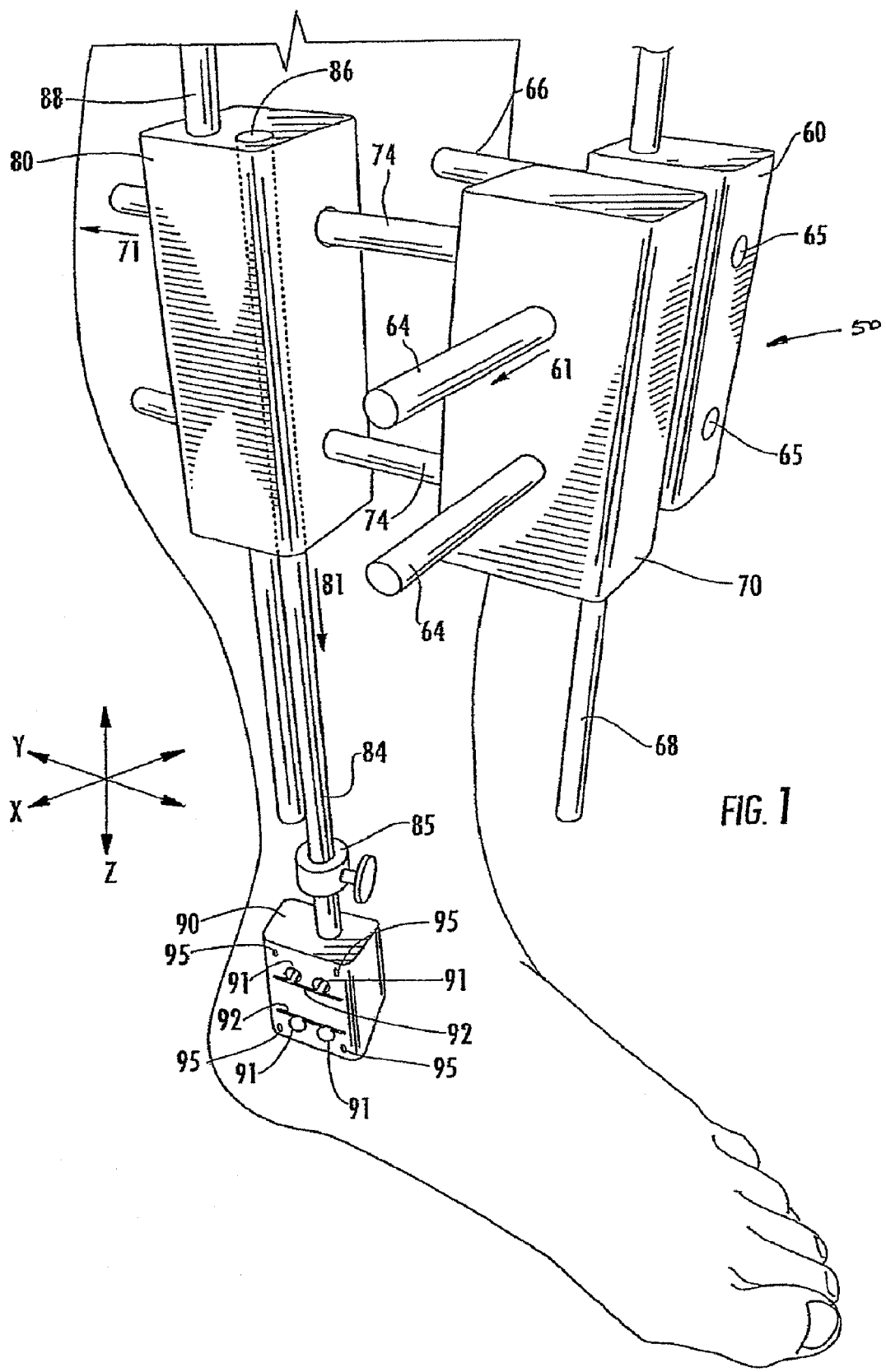
FIG. 1 is a perspective view of an embodiment of a cutting alignment apparatus in accordance with the present invention.

For purposes of the description hereinafter, the terms "upper", "lower", "right", "left", "vertical", "horizontal", "top", "bottom", "lateral", "longitudinal" and derivatives thereof shall relate to the invention as it may be oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as unduly limiting. For example, certain portions of the invention are shown as oblong blocks having circular holes positioned therethrough, which could be configured in a number of shapes and manners as various embodiments of the invention described herein.

As employed herein, the term "osteotomy" is employed in accordance with its traditional meaning to refer to the cutting or otherwise suitable removal or severing of bone.

As employed herein, the terms "cut" and "cutting" refer to the process of slicing, chiseling, or otherwise suitably removing or severing bone.

As employed herein, the terms "drill" and "drilling" refer to the process of creating a hole, bore or aperture in bone.

As employed herein, the term "cutting device" refers to any known or suitable tool or mechanism suitable for "cutting" bone.

As employed herein, the term "drilling device" or "drill" refers to any known or suitable tool (e.g., without limitation, drill bit) or mechanism for "drilling" bone.

As employed herein, the term "bone" refers to any known or suitable human, animal or artificial structure suitable for use in the body as a component of the skeleton.

As employed herein, the term "guide" refers to any known or suitable mechanism, apparatus or fixture (e.g., without limitation, jig), or suitable combination thereof, for establishing a predetermined desired relationship (e.g., suitably precise alignment) between two or more components in order to perform a procedure (e.g., without limitation, an osteotomy) in a suitably precise and accurate manner, which can be substantially replicated or reproduced.

As employed herein, the terms "fastener" and "fastening mechanism" refer to any known or suitable connecting, securing or tightening material, structure or device and expressly include, but are not limited to, suitable protrusions for securing one component to another, as well as receptacles (e.g., without limitation, recesses; slots; sockets; grooves), combinations of interlocking protrusions and receptacles, welds, and devices such as pins, rivets, screws, bolts and any suitable combination of bolts, nuts (e.g., without limitation, lock nuts) and/or washers.

As employed herein, the statement that two or more parts are "coupled" together shall mean that the parts are joined together either directly or joined through one or more intermediate parts.

As employed herein, the term "number" refers to the quantity one or an integer greater than one (i.e., a plurality).

As employed herein, the term "patient" shall mean human beings and other members of the animal kingdom.

As employed herein, the term "meniscus" shall mean any mobile bearing structure or surface between two other structures or surfaces, such as, for example, a meniscus insert between first and second joint components.

The present invention is directed to an ankle prosthesis, a method of preparing the ankle joint for replacement implementing such ankle prosthesis and an alignment apparatus that enables such replacement to be performed from a medial position on the ankle, as illustrated in various embodiments in FIGS. 1-21. In general, an ankle prosthesis 100 of the present invention is adapted for use in connection with the method of preparing the ankle joint for replacement, which may also implement a cutting alignment apparatus 50. As discussed hereinafter, the components of the ankle prosthesis 100 and the cutting alignment apparatus 50 provide a configurable and modifiable ankle replacement system and alignment therefore, allowing a patient receiving such method of ankle replacement to more effectively overcome the symptoms for which the arthroplasty procedure was performed.

Generally in arthroplasty procedures, an external fixator apparatus (not shown) may be applied to the area of interest to assist in normalizing and distracting the joint that is intended to undergo the medical procedure. More specifically, the external fixator apparatus is employed to distract the bones concerned with the ankle joints for positioning the ankle joint into proper alignment. In a preferred embodiment, the method of preparing the ankle joint includes applying the external fixator apparatus to the lateral side of the lower leg of the patient.

As is common in the art of arthroplasty procedures, pins, nails or screws may be placed into the tibia 20, the talus 40 and the calcaneus 36. The external fixator apparatus may be actuated to separate the tibia 20 from the talus 40 a sufficient distance such that the proper alignment is achieved in order to perform the remaining steps of the method of preparation of the present invention. However, the final separation will be determined by the medical professional implementing such external fixator apparatus based upon the symptoms of the patient and the diagnosis of the medical professional that will best accomplish a successful arthroplasty procedure. After the arthroplasty procedure is completed, the external fixator may be distracted slowly until the ankle joint is in the proper alignment and pain is relieved. When the medical professional is satisfied that distraction is no longer necessary, the external fixator may be removed.

Figure 5:
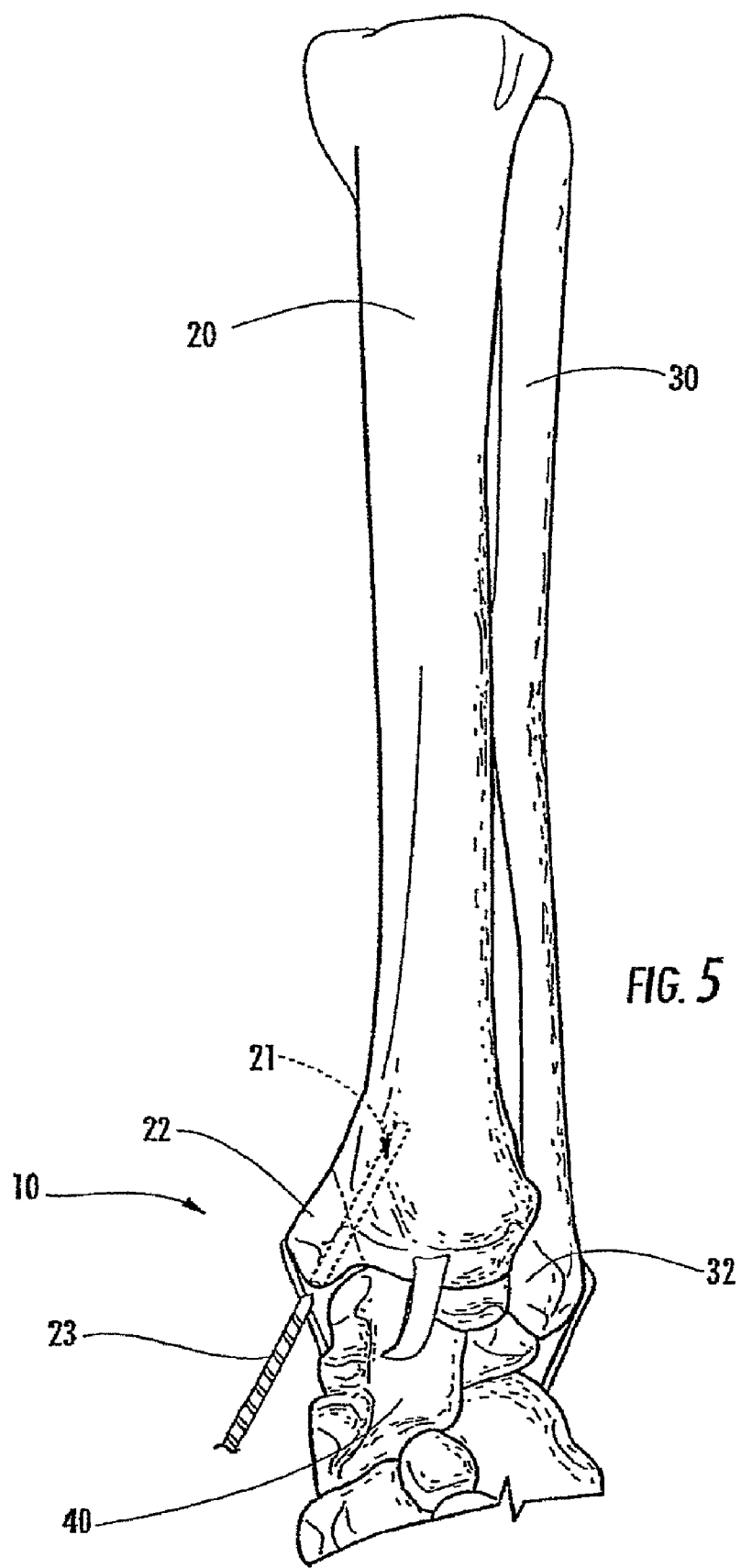
FIG. 5 shows a front elevational view of an embodiment of a preparation step for the medial portion of the tibia in accordance with the present invention.
Figure 6:
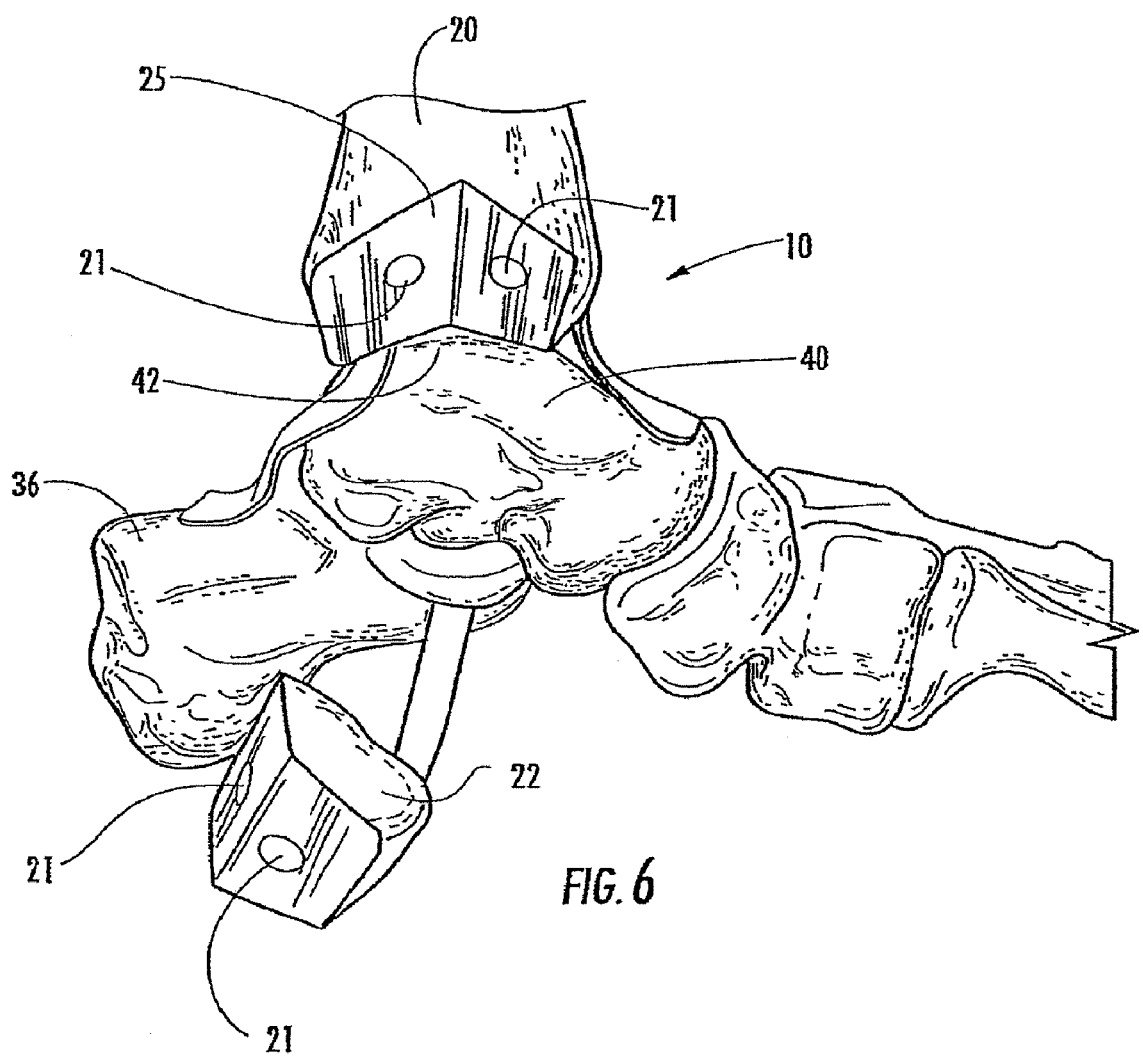
FIG. 6 illustrates a lateral view of an ankle that has undergone an embodiment of a preparation step for the medial portion of the tibia in accordance with the present invention.

As can be seen in FIG. 5, the method of preparation includes the forming of alignment apertures 21 into the medial portion 22 of the tibia 20. The forming of the alignment apertures 21 may be accomplished in a number of ways including, but not limited to, drilling, boring, etc. with a tool 23. In a preferred embodiment, at least two alignment apertures 21 may be formed in the medial portion 22 of the tibia 20 as illustrated in FIG. 6. However, due to varied circumstances it may only be necessary in certain instances to form one alignment aperture 21 in an appropriate location such as, for example, in the vicinity of the valley of the chevron osteotomy discussed in greater detail below.

The method further includes an osteotomy of the medial portion 22 of the tibia 20. In a preferred embodiment, the osteotomy is performed forming tibial chevron section 25 where the medial portion 22 of the tibia 20 is removed as shown in FIG. 6. In order to perform such osteotomy, the posterior tibial tendon retinaculum and superficial deltoid may be taken down such that the medial portion 22 of the tibia 20 may be removed as illustrated in FIGS. 6-6b.

Figure 6A:
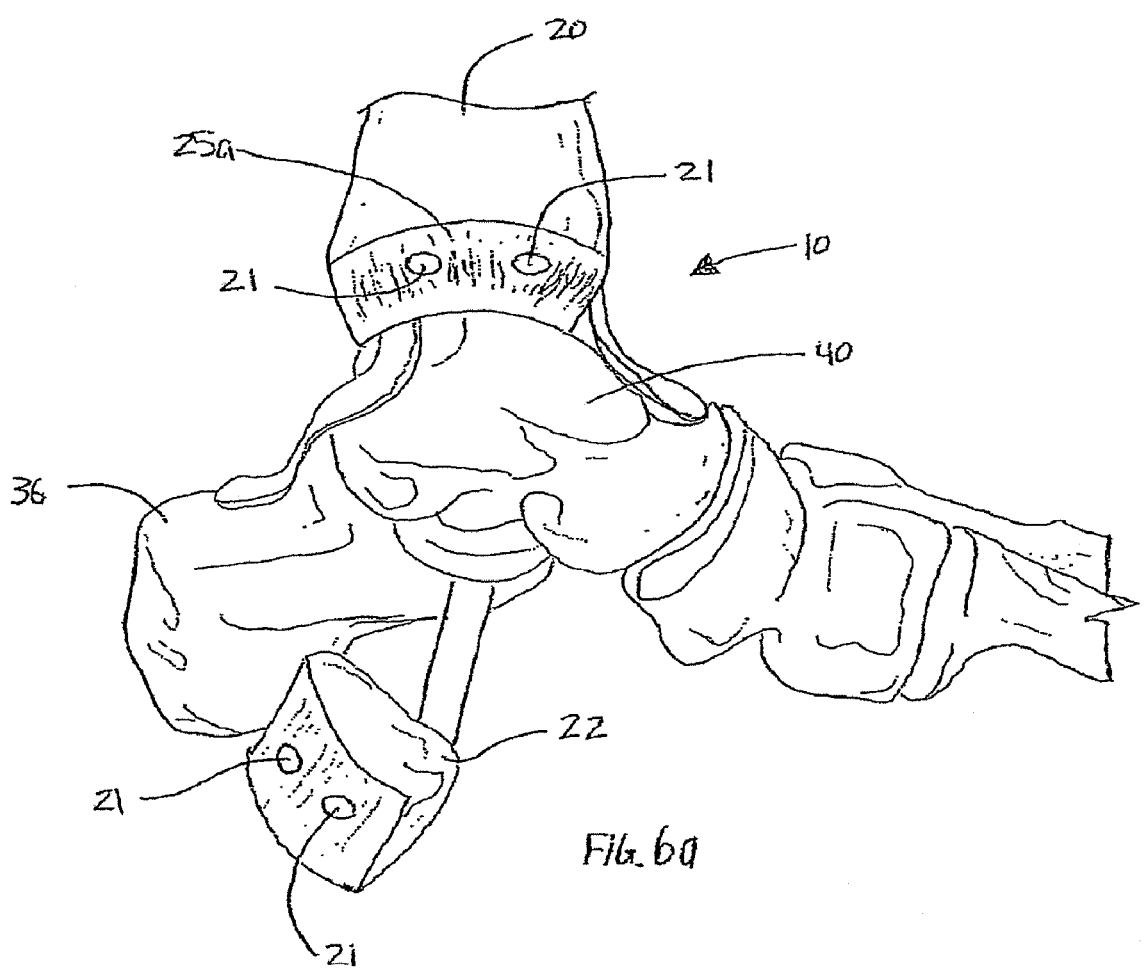
FIG. 6a illustrates a lateral view of an ankle that has undergone an embodiment of a preparation step for the medial portion of the tibia in accordance with the present invention.

Further, as can be seen in FIGS. 6a and 6b, more than one type of osteotomy may be performed on the medial portion 22 of the tibia 20 in accordance with the invention. For example, as shown in FIG. 6a, a crescentic section 25a may be removed by using a crescentic saw blade to perform the osteotomy. Similarly, as also generally shown in FIG. 6a, a circular section 25a may be removed by using a biradial saw blade. A further example of the osteotomy that may be performed, as determined by the medical professional implementing such method of preparation according to the present invention, is a valley section 25b as illustrated in FIG. 6b. Accordingly, any number of osteotomies may be performed, as may be determined by the medical professional based upon the composure and integrity of the medial portion 22 of the tibia 20 specific to the patient undergoing such method of preparation may be used in accordance with the present invention.

Figure 8:
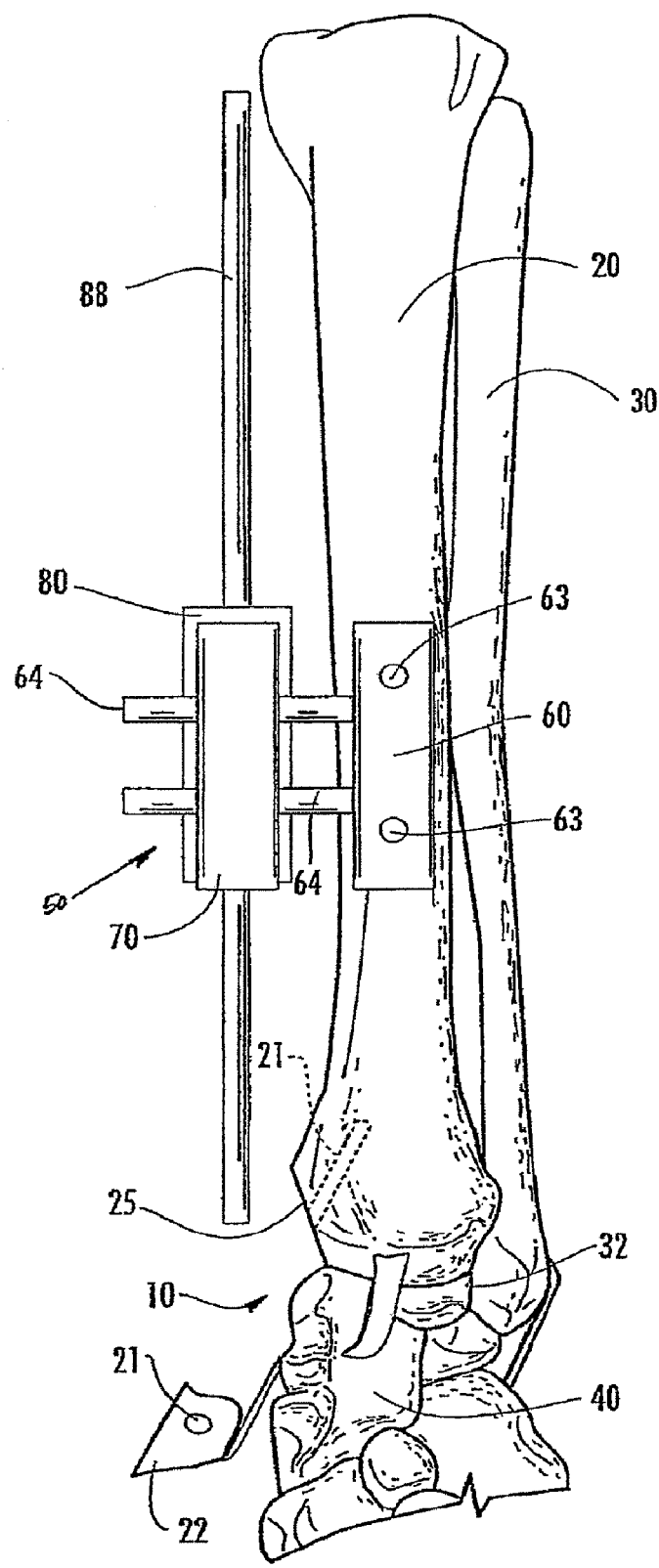
FIG. 8 is a front elevational view of an embodiment of a second and third positioner, having an alignment rod positioned therethrough, as they may be positioned in accordance with the present invention.
Figure 11:
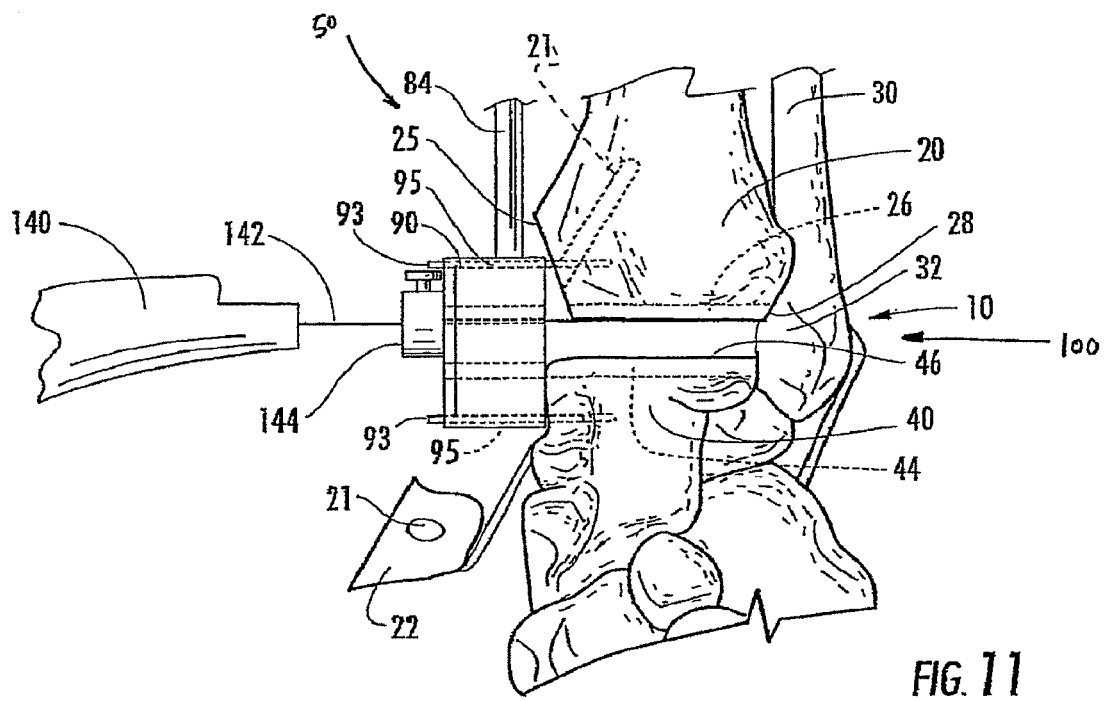
FIG. 11 is a front elevational view of an embodiment of a preparation step for the tibia and the talus in accordance with the present invention.
Figure 12:
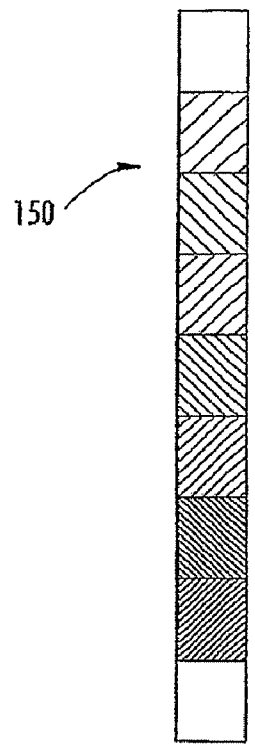
FIG. 12 is a plan view of an embodiment of a measuring implement in accordance with the present invention.
Figure 13:
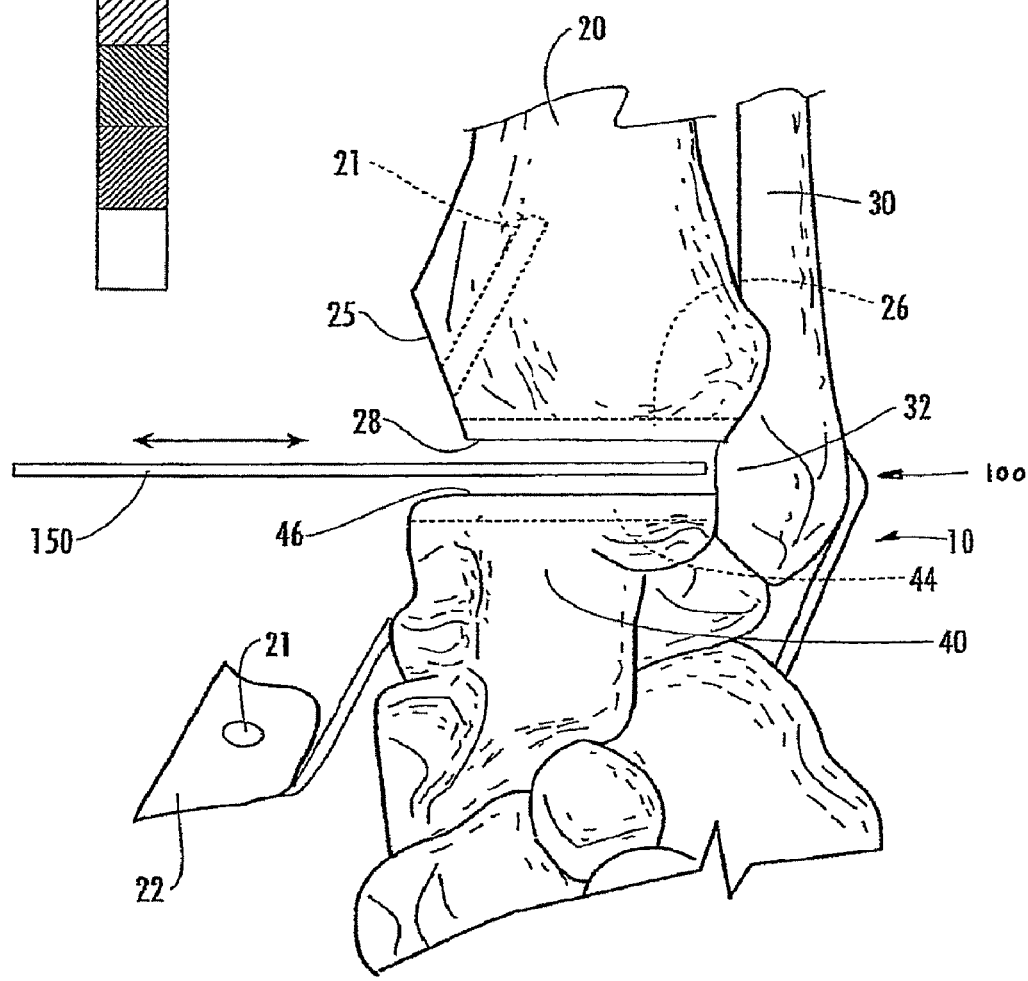
FIG. 13 illustrates a front elevational view of an embodiment of a preparation step utilizing the measuring implement in accordance with the present invention.
Figure 17:
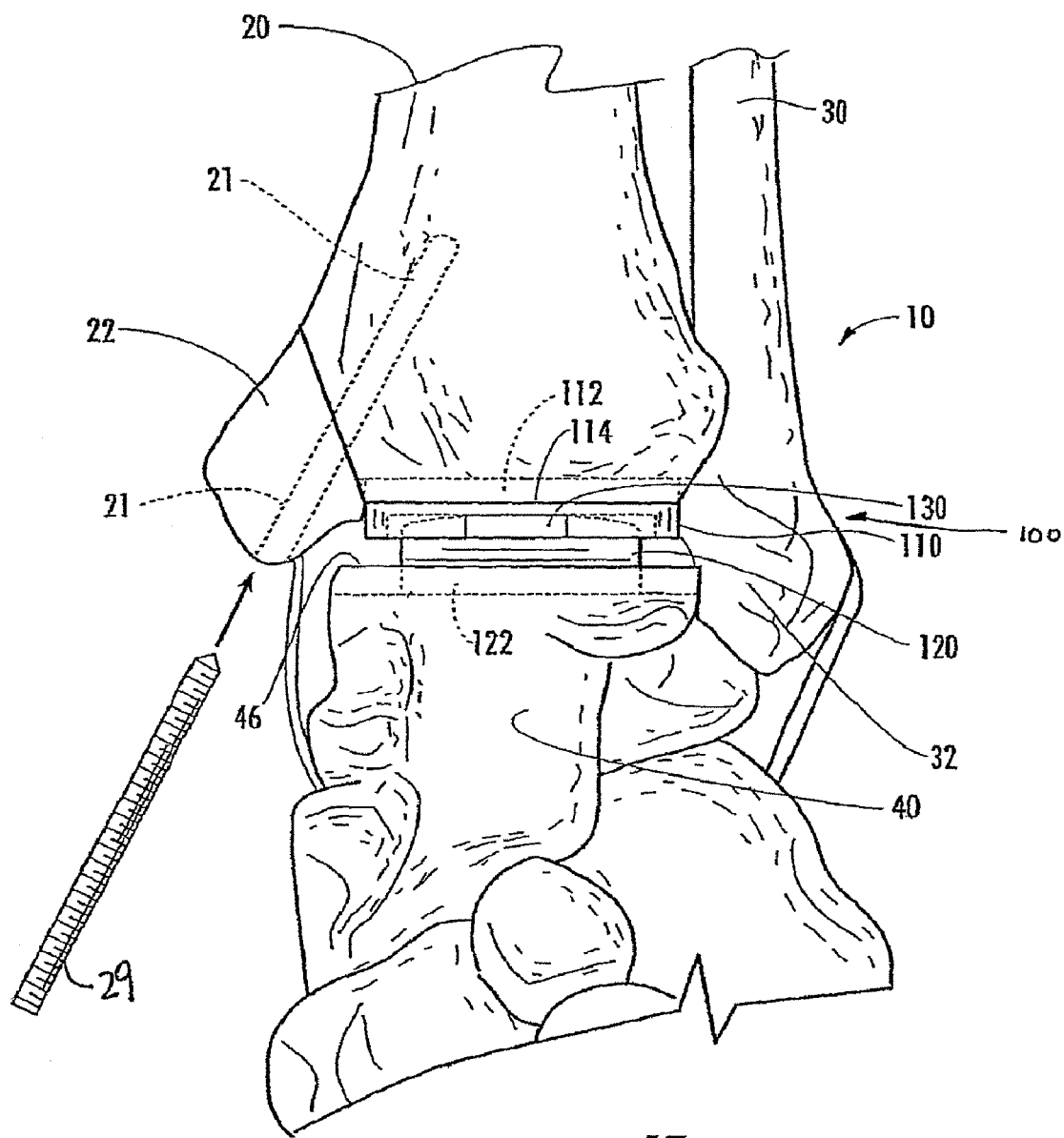
FIG. 17 is a front elevational view illustrating an embodiment of an inserted ankle replacement and a preparation step for the medial portion of the tibia in accordance with the present invention.
Figure 18:
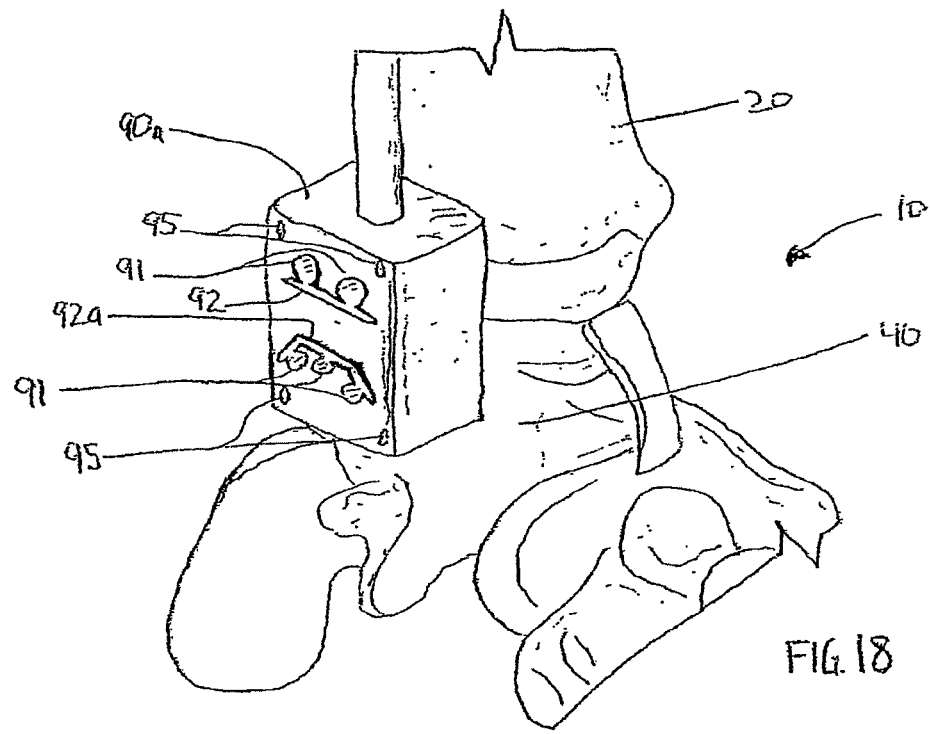
FIG. 18 is a perspective view of an embodiment of a cutting guide in accordance with the present invention.
Figure 19:
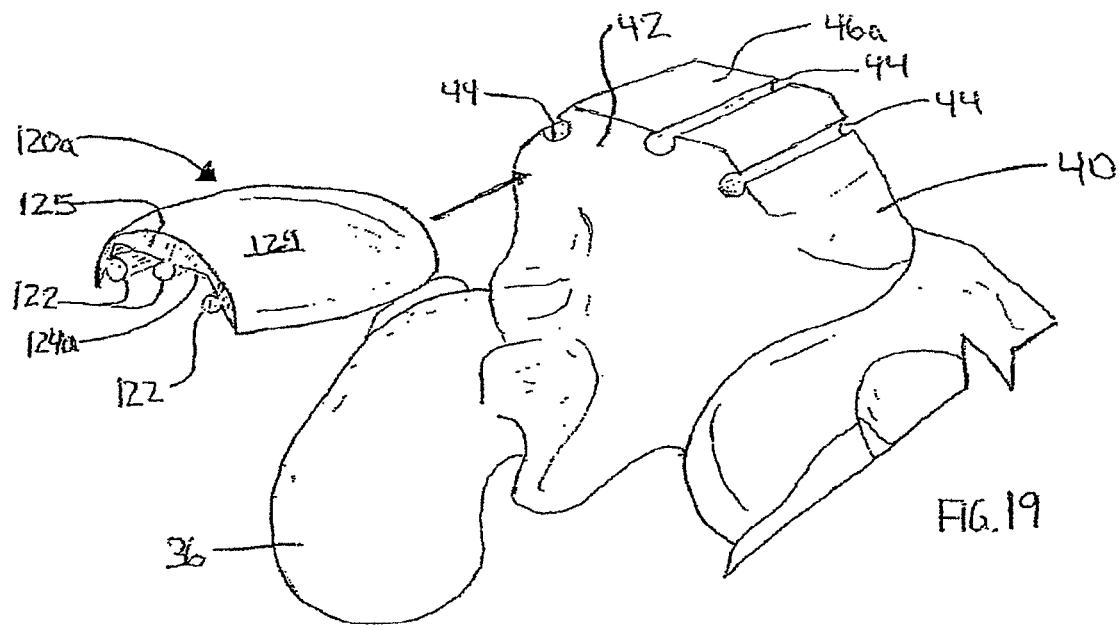
FIG. 19 illustrates a perspective view of an embodiment of a talar component of an ankle replacement as it may be positioned in accordance with the present invention.
Figure 20:
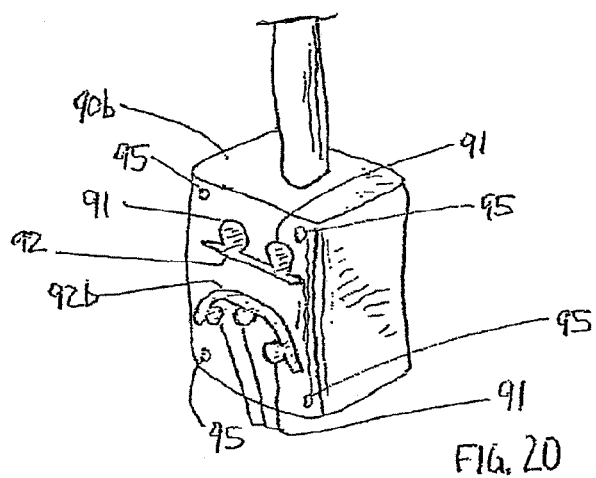
FIG. 20 is a perspective view of an embodiment of a cutting guide in accordance with the present invention.
Figure 21:
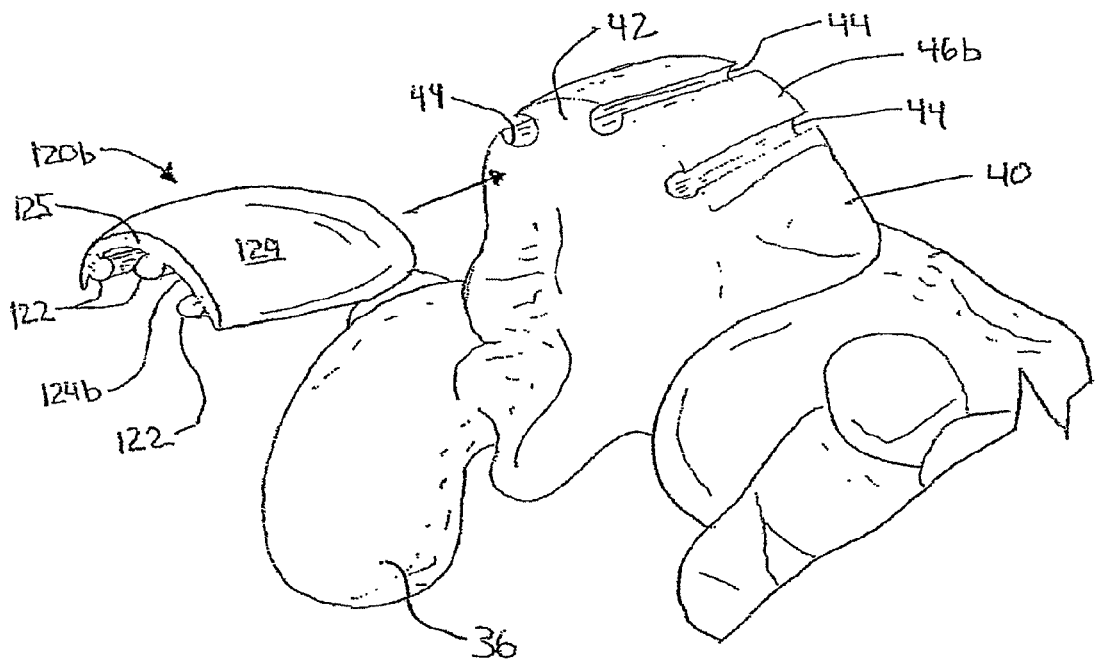
FIG. 21 is illustrates a perspective view of an embodiment of a talar component of an ankle replacement as it may be positioned in accordance with the present invention.

Next, a lateral incision (not shown) may be made over a distal portion 32 of the fibula 30 which is shown in FIG. 8. The incision may be made such that the syndesmosis located in this area of the ankle may be exposed. A dissection may then be performed such that at least the inferior aspect of the syndesmosis may be taken down. This may further expose the distal portion 32 of the fibula 30 to assist in performing the arthroplasty procedure and preventing unnecessary damage to the distal portion 32 of the fibula 30. For example, exposing this area visually enables prevention of damage from over cutting, as will be described in greater detail below, and may also provide access to the lateral side of the ankle for assisting in positioning the ankle prosthesis 100 as can be seen in FIGS. 11, 13 and 17.

The cutting alignment apparatus 50, and components thereof, is illustrated generally in FIGS. 1-4 and 7-11 for assisting in performing an arthroplasty procedure as will be discussed in greater detail below. The main components of the cutting alignment apparatus 50 include a first positioner 60, a second positioner 70 and a third positioner 80. As can be seen in the drawings, a cutting guide 90 may also be attached in order to perform embodiments of the ankle preparation method described herein. Although the cutting alignment apparatus 50 is separable for convenience in sterilizing the cutting alignment apparatus 50, in accordance with the present invention, the cutting alignment apparatus 50 may also be unitary provided it allows for the same functionality. Accordingly, when component portions of the cutting alignment apparatus 50 are discussed, it is herein understood that other portions of the cutting alignment apparatus 50 may also be physically attached during these steps.

For purposes of describing the cutting alignment apparatus 50, several components of the cutting alignment apparatus 50 will be described based upon their interspatial relations with other components. Accordingly, a first direction 61, a second direction 71 and a third direction 81 will be used to describe these interrelated components. As viewed in FIG. 1, the first direction 61 is indicated with an arrow and corresponds with the indicated direction with reference to the X axis generally. Likewise, the second direction 71 is also indicated with an arrow and corresponds with the direction indicated by the arrow in reference to the Y axis generally. The third direction 81 is also indicated with an arrow and corresponds with the direction indicated with reference to the Z axis generally. Again, these dimensional descriptions related to the embodiments disclosed herein are not to be considered as unduly limiting but are merely used for the purpose of describing embodiments of the general interspatial relations of the components of the present invention.

The first positioner 60 may be utilized for accomplishing several attributes of alignment with regards to the expected positioning of components that comprise the ankle joint. In particular, referring to FIGS. 1, 2 and 7, the first positioner 60 may have an apparatus alignment rod 68 positioned within an alignment rod aperture 67. The alignment rod aperture 67 may be positioned through the first positioner 60 generally vertically or in a direction with reference to the Z axis. Accordingly, the alignment rod 68 may be retained within the alignment rod aperture 67 to assist in alignment of the ankle 10 with respect to various alignment orientations such as, for example, varus/valgus alignment.

Once alignment of the first positioner 60 is determined, first alignment extensions 66 of the first positioner 60 may be used to locate the tibia 20. First alignment extensions 66 extend from the first positioner 60 in the second direction 71 generally. The first positioner 60 may also have securing member apertures 65 extending through the first positioner 60 in the second direction 71 as well. The securing member apertures 65 preferably do not intersect with the first alignment extensions 66, although it is possible provided that alignment extensions 66 do not interfere with elements positioned within securing member apertures 65 such as, for example, where alignment extensions 66 are removable or repositionable to prevent interference. Alternatively, securing member apertures 65 may not be necessary and thus would not be present in the first positioner 60, as will be discussed in greater detail below.

Figure 7:
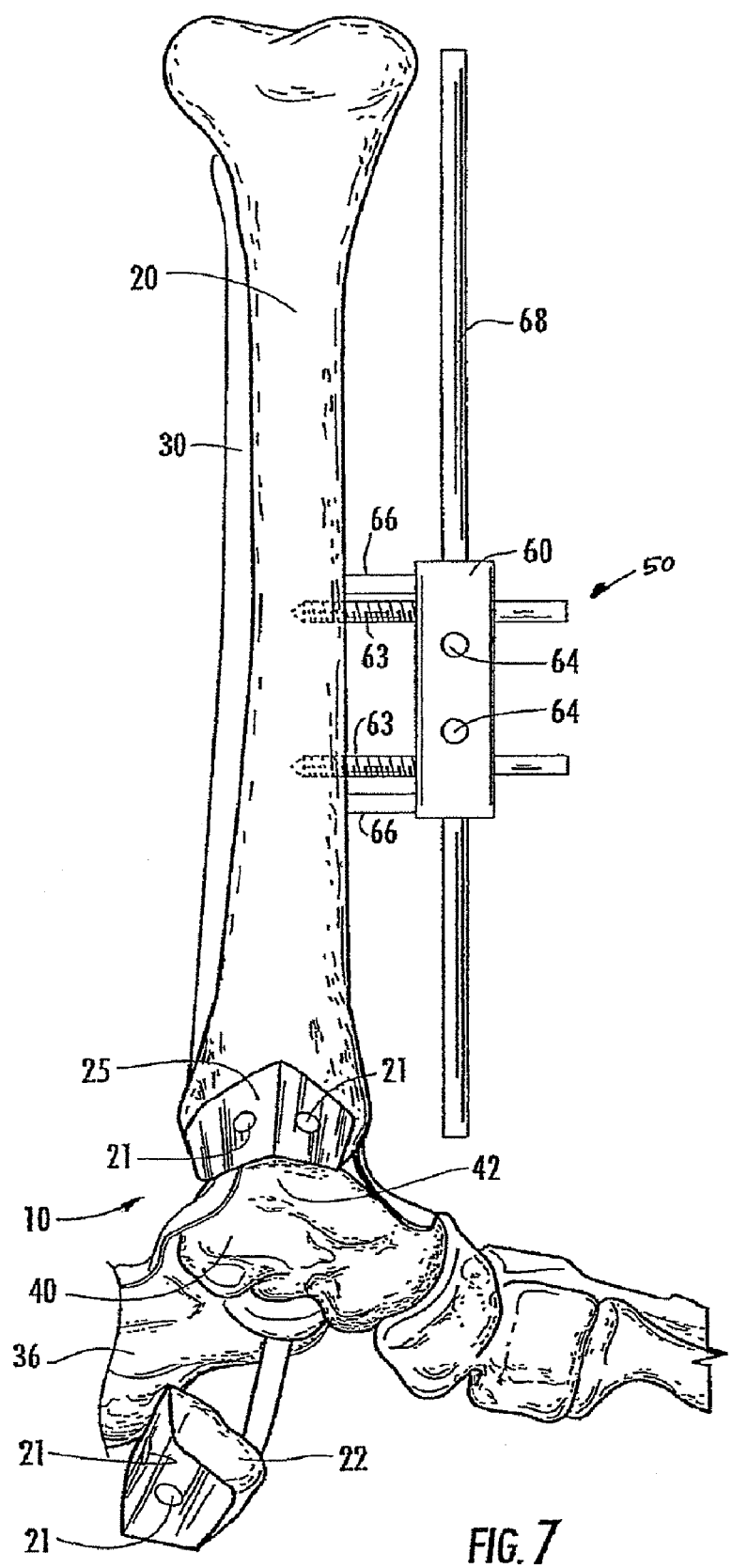
FIG. 7 is a lateral elevational view of an embodiment of a first positioner, having an alignment rod positioned therethrough, as it may be secured to the tibia in accordance with the present invention.

While first alignment extensions 66 are resting on the tibia 20 with the first positioner 60 in the desired aligned orientation, securing members 63 may be inserted into the tibia 20 through securing member apertures 65 as illustrated in FIGS. 7 and 8. Securing members 63 may generally comprise pins, nails or screws that may be secured into the tibia 20, thus securing the first positioner 60 in place. However, as mentioned above, securing apertures 65 may not be necessary as alternative securing means (not shown) may be implemented in place of securing members 63. For example, a medical professional may determine to perform the method of preparation implementing bone clamps (not shown) or securing straps (not shown) to secure the first positioner 60 in place.

The first positioner 60 has first rods 64 extending from the first positioner 60 in the first direction 61. The first rods 64 may be used to connect the first positioner 60 to the second positioner 70, unless second positioner 70 is already connected in a unitary embodiment. The first positioner 60, first rods 64 and first alignment extensions 66 may be constructed of any suitable materials able to undergo the sterilization processes required for surgical instrumentation. Further, first rods 64 and first alignment extensions 66 may or may not be detachable from the first positioner 60 depending upon the desired orientation of the cutting alignment apparatus 50 and restrictions of the required sterilization processes and equipment.

The second positioner 70 has second rods 74 extending in the second direction 71 from the second positioner 70. The second positioner 70 also has second apertures 72 extending through the second positioner 70 in the first direction 61. Thus, the first rods 64 may be positioned within the second apertures 72 to connect the second positioner 70 to the first positioner 60. The second positioner 70 may then be in communication with the first positioner 60 accordingly. In a preferred embodiment, the second positioner 70 will be adjustably engaged with the first positioner 60 such that the second positioner 70 may be translated along first rods 64 to be positioned appropriately for the overall alignment of the cutting alignment apparatus 50. For example, the second positioner 70 may slide along first rods 64 to allow adjustability. The second rods 74 and second positioner 70 may likewise be constructed of any suitable materials able to undergo the sterilization processes required for surgical instrumentation and may or may not be detachable from one another.

The third positioner 80 has third apertures 82 extending through the third positioner 80 in the second direction 71. The second rods 74 may be positioned within the third apertures 82. Again, the positioning of the second rods 74 within the third apertures 82 may form the connection between the second and third positioners 70, 80 in the separable embodiment of the invention or otherwise may already be thus positioned in the unitary embodiment. Thus, the third positioner 80 may be in communication with the second positioner 70 via the second rods 74 positioned within the third apertures 82. In a preferred embodiment, the third positioner 80 may also be adjustably engaged with the second positioner 70 in a similar manner as the connection between the first and second positioners 60, 70 providing translation of the third positioner 80 in order to properly position the third positioner 80 for the overall alignment of the cutting alignment apparatus 50.

The third positioner 80 also has a fourth aperture 86 extending through the third positioner 80 in the third direction 81. A third rod 84 may be positioned within the fourth aperture 86 that may be removable or merely adjustable within the fourth aperture 86 as in the unitary embodiment. At the end of the third rod 84, the cutting guide 90 may be positioned. Accordingly, the cutting guide 90 may be in communication with the third positioner 80 such that the cutting guide 90 may be adjusted, or translated, along at least the Z axis with reference to the third direction 81. In order to assist in maintaining the desired position of the cutting guide 90, at least one adjustor 85 may be employed. Adjustor 85 may be a fine screw to allow for fine adjustments along the Z axis or may otherwise be a course position holder used to secure third rod 84 in a desired position. The cutting guide 90 may also be permitted to rotate about the Z axis in order to permit further adjustment if necessary.

The third positioner 80 may be utilized for accomplishing several attributes of alignment with regards to the desired positioning of the cutting guide 90 and the position of the lower leg and ankle joint generally. In particular, referring to FIGS. 1, 4 and 8, the third positioner 80 may have a cutter alignment rod 88 positioned within a cutter alignment rod aperture 87. The cutter alignment rod aperture 87 may be positioned through the third positioner 80 generally vertically or in a direction with reference to the Z axis. The cutter alignment rod 88 may thus be retained within the cutter alignment rod aperture 87 to assess the alignment of the ankle 10 and lower leg with respect to various alignment orientations such as, for example, procurvation/recurvation alignment. Once the alignment of the ankle 10 and lower leg is diagnosed through the use of the cutter alignment rod 88, the cutting guide 90 may be positioned more accurately to the desired orientation.

The third positioner 80, third rod 84, cutter alignment rod 88, adjustor 85 and cutting guide 90 may all be constructed of any suitable materials able to undergo the sterilization processes required for surgical instrumentation and may or may not be detachable from one another.

As shown in FIGS. 9-11, 14 and 15 in a preferred embodiment, the cutting guide 90 is specifically configured to be implemented with the particular mounting portions 1 12,122 of the ankle prosthesis 100. Accordingly, the cutting guide 90 is provided with mount cut apertures 91 that correspond with mounting portions 112,122 of the ankle prosthesis 100. Other mounting configurations may require differing mount cut apertures depending upon the configuration of alternate mounting portions in accordance with the present invention. For example, alternate embodiments may include triangular mounting portions 112b, cross mounting portions 112c, etc. as opposed to cylindrical mounting portions 112,122 as will be discussed in greater detail below.

As can be seen in FIGS. 1, 4 and 9-11, the cutting guide 90 has cutting slots 92 positioned therethrough. Cutting slots 92, in the preferred embodiment, are of a sufficient length to permit adequate cutting of the section of bone to be removed. In addition, the cutting slots 92 have a sufficient height to permit a blade 142 of a saw 140 to pass therethrough while guiding the blade 142 along the desired orientation of the cutting guide 90. Accordingly, the cutting slots 92 are positioned to ensure the proper cut once the cutting guide 90 is aligned.

Before the cutting step begins, the cutting guide 90 may be secured to the tibia 20 to ensure the cutting guide 90 is properly positioned. Thus, cutting guide 90 may be provided with cutting securing member apertures 95 positioned therethrough. Accordingly, cutting securing members 93 may affix the cutting guide 90 to the ankle 10 to ensure a proper cutting location insertion into the bone of the ankle 10. Securing members 93 may comprise nails, screws, pins etc. Again, as with the first positioner 60, cutting guide 90 may be secured to ensure proper cutting orientation in other fashions in accordance with the present invention. For example, a medical professional may determine to perform the method of preparation implementing bone clamps (not shown) or securing straps (not shown) to secure the cutting guide 90 in place.

The method may further include the use of retractors (not shown) before the cutting step. Retractors are generally known in the surgical arts and may be implemented to hold back the edges of the surgical incision made on the medial area of the ankle 10.

As suggested above, protectors (not shown) may be inserted into the area exposed near the distal portion 32 of the fibula 30 to prevent unnecessary damage that may occur from over cutting. In addition, a stop 144 may be implemented on the blade 142 of the saw 140 to prevent over cutting.

Figure 9:
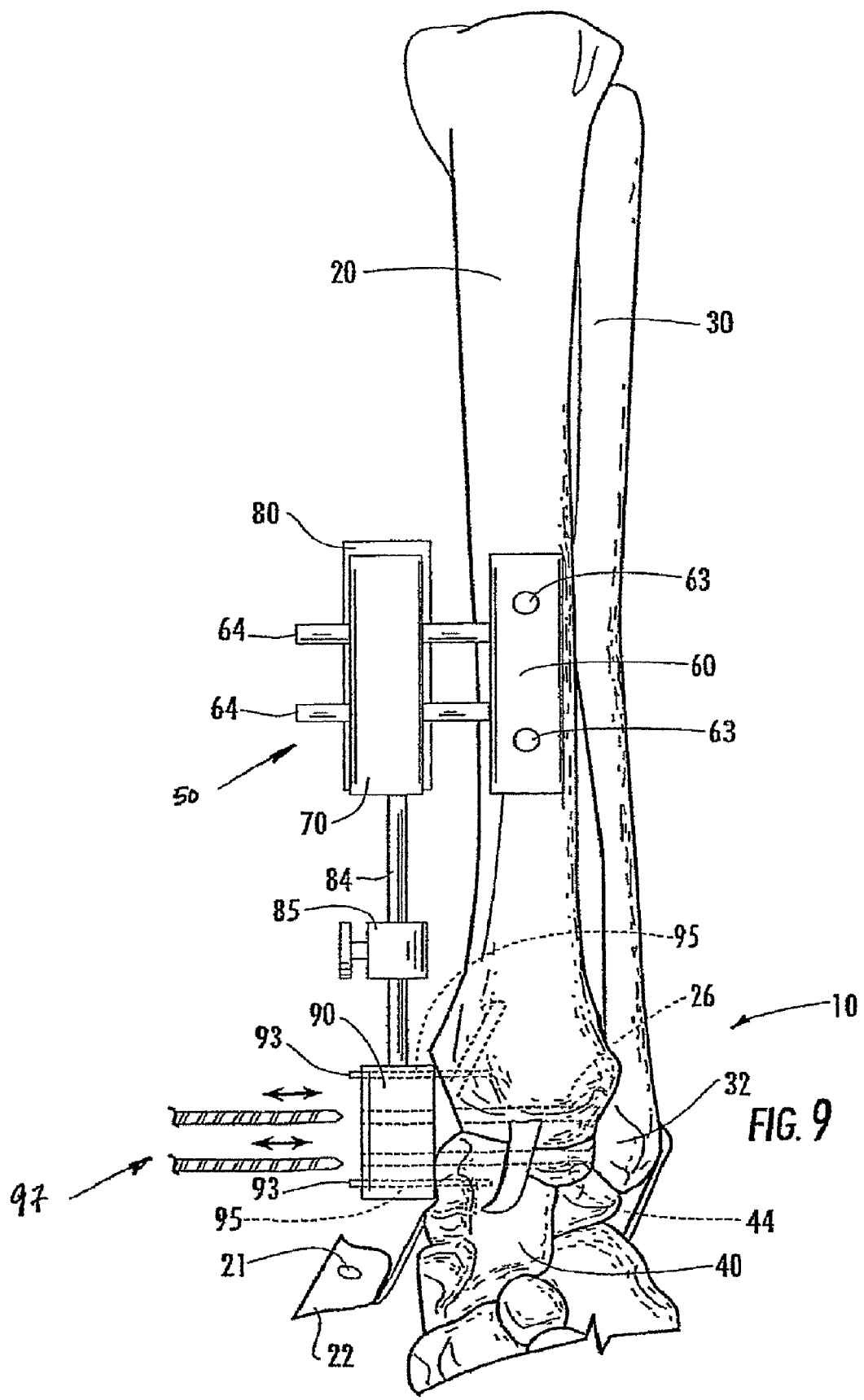
FIG. 9 shows a front elevational view of an embodiment of a preparation step for the tibia and talus in accordance with the present invention.
Figure 14:
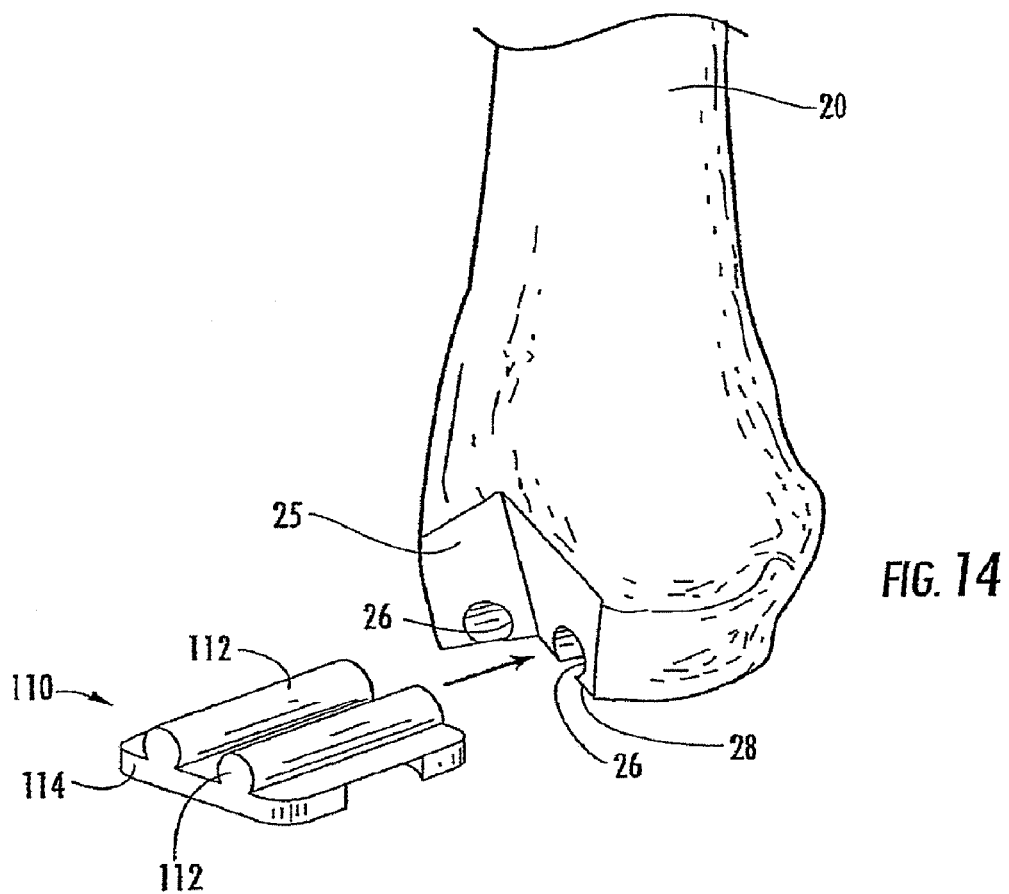
FIG. 14 shows a perspective view of an embodiment of a tibial component of an ankle replacement as it may be positioned in accordance with the present invention.
Figure 14A:
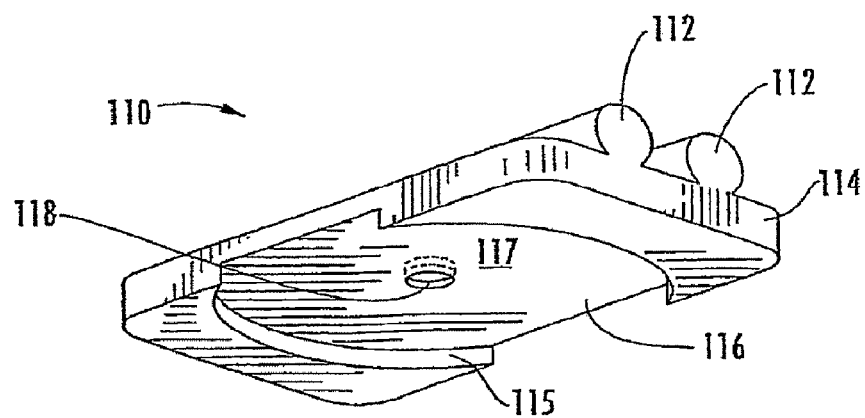
FIG. 14a is a perspective view of an embodiment of a tibial component of an ankle replacement in accordance with the present invention.
Figure 15:
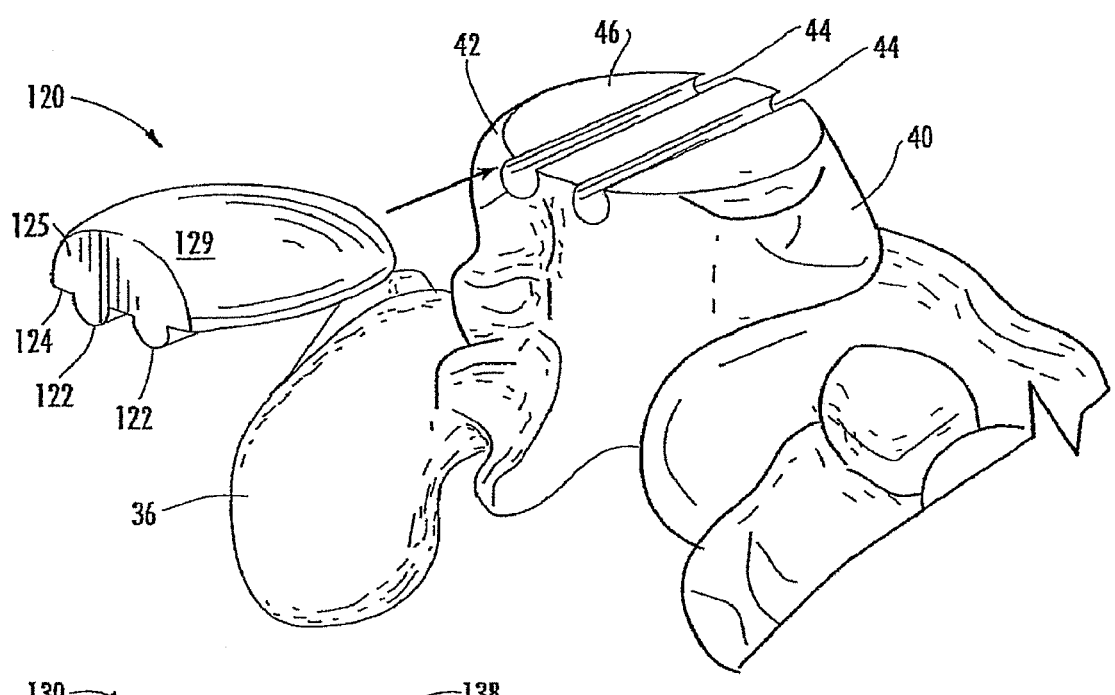
FIG. 15 illustrates a perspective view of an embodiment of a talar component of an ankle replacement as it may be positioned in accordance with the present invention.

Referring to FIGS. 9-11 and 13, the preparation of the tibia 20 and talus 40 of ankle 10 to receive the ankle prosthesis 100 is shown. As can be seen in FIG. 9, a tool such as, for example, a drill 97 may be used with the cutting guide 90 to form a tibial mounting recess 26 in the tibia 20. The drill 97 is positioned within the mount cut aperture 91 and inserted into the tibia 20 a desired depth. Various methods to control the depth may be implemented including, but not limited to, a stop (not shown) on the drill, a mark on the drill 97 indicating the desired depth, etc. As can be seen in FIG. 14, the tibial mounting recesses 26 will provide a configuration to which the ankle prosthesis 100 may be secured. Likewise, the drill 97 may also be inserted into the lower mount cut apertures 91 a desired depth to form a talar mounting recess 44 in the talar dome 42 as shown in FIGS. 9 and 15.

Figure 14B:
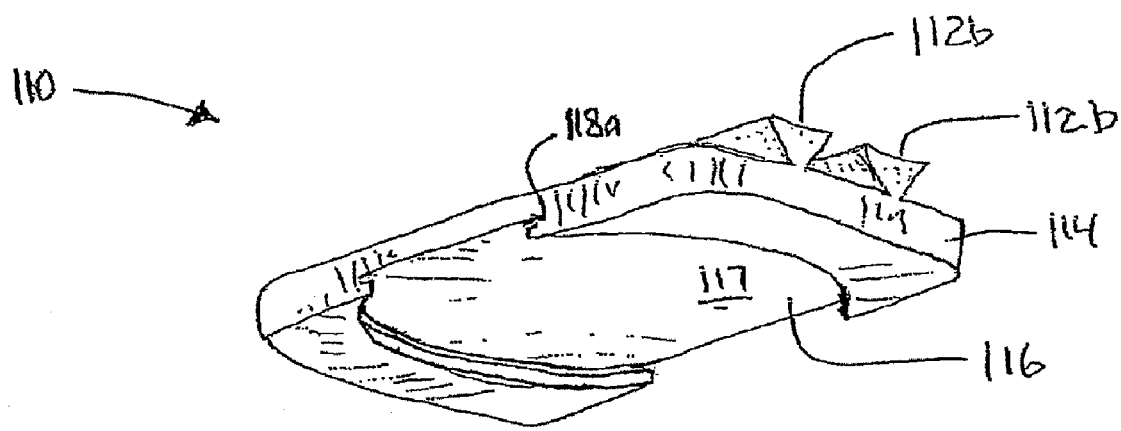
FIG. 14b is a perspective view of an embodiment of a tibial component of an ankle replacement in accordance with the present invention.
Figure 14C:
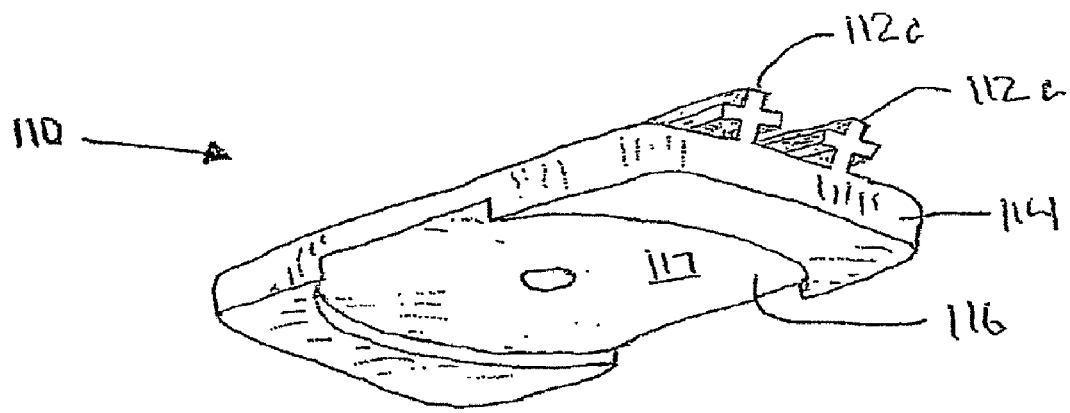
FIG. 14c is a perspective view of an embodiment of a tibial component of an ankle replacement in accordance with the present invention.

As discussed above, alternate embodiments may include triangular mounting portions 112b, cross mounting portion 112c, etc., as opposed to cylindrical mounting portions 112, 122 and illustrated in FIGS. 14b-14c. Likewise, triangular mounting portions and, cross mounting portions (similar to portions 112b,112c) may also be implemented in a similar fashion with other mounting components of the ankle prosthesis 100 (i.e., talar mounting component 120 discussed below). Accordingly, other tools may be used to form mounting recesses that conform to the mounting portions of the ankle prosthesis 100 selected by the medical professional. In addition, the cutting guide will also be provided with mount cut apertures that correspond with the desired shape of mounting recesses in accordance with present invention.

With the cutting guide 90 secured to the ankle 10, and the mounting recesses 26,44 formed, the osteotomy of the tibia 20 and talar dome 42 may be performed using the saw 140 positioned through the cutting slots 92. Although in the preferred embodiment the mounting recesses 26,44 are formed before the osteotomy of the tibia 20 and talar dome 42, these steps may be reversed as preferred by the medical professional implementing such method of preparation according to the present invention.

Figure 10:
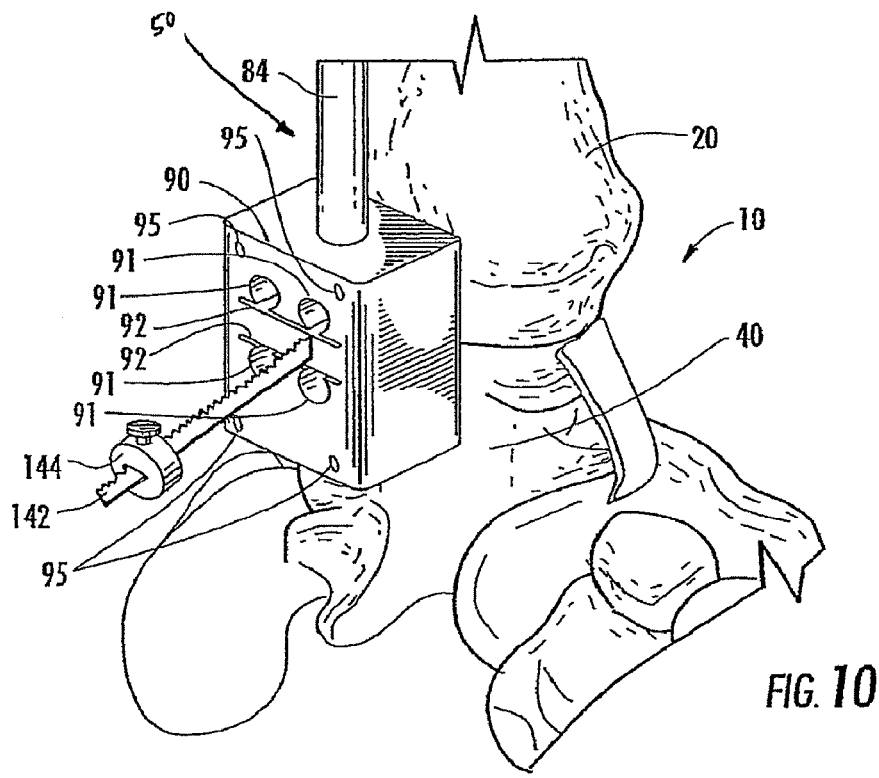
FIG. 10 is a perspective view of a saw as it may be used with an embodiment of a cutting guide in accordance with the present invention.

FIGS. 10 and 11 illustrate the saw blade 142 as it may be utilized to make a generally straight cut to form tibial section 28 and a talar section 46. In the preferred embodiment, the tibial section 28 will intersect the tibial mounting recess 26 and the talar section 46 will intersect the talar mounting recess 44. Such intersection will better prepare the ankle 10 to receive the ankle prosthesis 100.

A measuring device 150 may be employed to determine the appropriate size of the ankle prosthesis 100. As can be seen in FIG. 13, the measuring device 150 is used to measure the dimensions of the tibial section 28 as well as the talar section 46. The measuring device 150 may be made of any suitable materials as are consistent with the requirements of the sterilization processes required. Further, the measuring device 150 may use any scale, as indicated by the shading in FIG. 12, necessary to best correlate that measurement with the appropriate sized ankle prosthesis 100.

As shown in FIGS. 14, 14a, 15, 16 and 17, the ankle prosthesis 100 may include a tibial component 110, a talar component 120 and a meniscus insert 130. When positioned together in the preparation of an ankle replacement, they function to serve the patient as an artificial ankle. The tibial component 110 is impacted into tibial mounting recesses 26, as shown in FIG. 14, using conventional methods known in the art. For example, as will vary by medical professional and standards set by the FDA, the tibial component insert 110 may be cemented into the tibia 20 or otherwise secured as required by regulation. Likewise, as can be seen in FIG. 15, the talar component 120 may be impacted into the talar mounting recesses 44.

The tibial component 110 of the ankle prosthesis 100 is generally formed out of a plate 114 having the tibial mounting portions 112 formed in the top of the plate 114. The plate 114 may be treated or otherwise texturized to better assist in the acceptance of the ankle prosthesis with the bone. On the opposing side of the plate 114 from the tibial mounting portions 112 is formed a recess 116 having inner walls 115 and a recessed surface 117. Recess 116 is provided to receive the meniscus insert 130 shown in FIG. 16. Within the recess 116 and extending toward the tibial mounting portions 112 into the plate 114, is formed an attachment recess 118 in the recessed surface 117. The tibial component 110 may be made of suitable materials capable of sterilization requirements and biomedical requirements for use with resected bone material. Several alloy metal materials are contemplated such as, for example, cobalt-chromium alloy, in the preferred embodiment having a surface treatment to ensure their smooth yet hard surface. However, any suitable material may be used as required for the given application and factors taken into consideration for the receiving patient.

Figure 16:
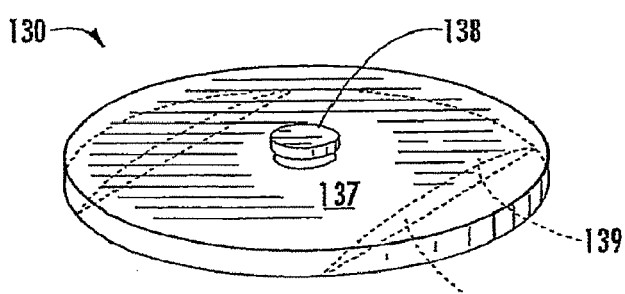
FIG. 16 is a perspective view of an embodiment of a meniscus insert of an ankle replacement in accordance with the present invention.

The meniscus insert 130, as illustrated in FIG. 16, has an attachment protrusion 138 that may take the form of a knob, a sphere, a cone having its circular cross section position on a post, etc. The attachment protrusion 138 in the preferred embodiment includes a disk-like shape positioned on a post. The meniscus insert 130 thus attaches to the tibial component 110 by inserting the attachment protrusion 138 into the attachment recess 118 of the tibial component 110. Once attached, the meniscus insert 130 should not be able to be removed from the tibial component 110 in the preferred embodiment. Further, in many preparation methods implemented according to the present invention, it may be preferable to attach the meniscus insert 130 to the tibial component 110 before impaction of the tibial component 110. In the preferred embodiment, ultra-high molecular-weight polyethylene (UHMWPE) may be used to form the meniscus insert 130 although other suitable materials may be implemented.

Figure 16A:
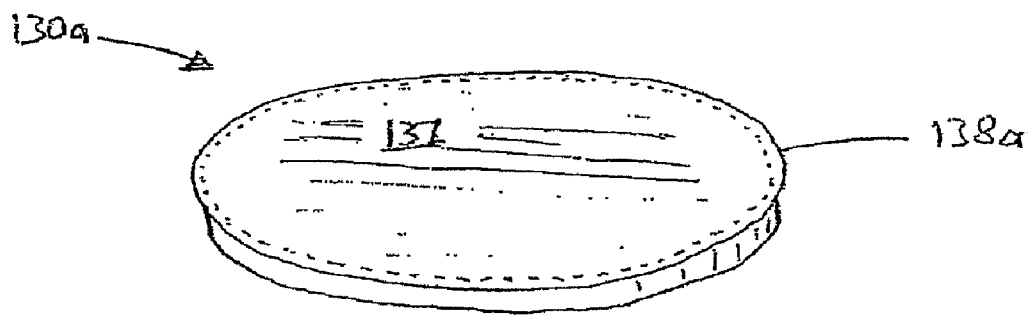
FIG. 16a is a perspective view of an embodiment of a meniscus insert of an ankle replacement in accordance with the present invention.
Figure 16B:
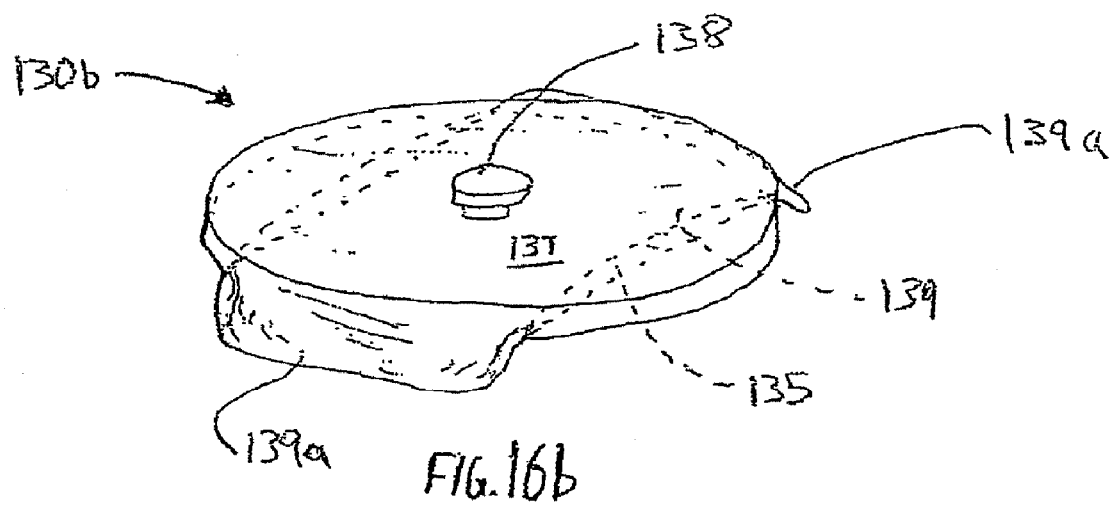
FIG. 16b is a perspective view of an embodiment of a meniscus insert of an ankle replacement in accordance with the present invention.

Multiple shapes maybe used to accomplish the securing of a meniscus insert 130 to the tibial component 110 that are contemplated within the scope of the present invention. For example, as shown in FIG. 16a, the attachment protrusion 138a may consist of a ridge that engages an attachment recess 118a of the tibial component 110. See FIG. 14b. In this embodiment, the ridge 138a may fit within the attachment recess 118a to secure the meniscus insert 130a to the tibial component 110. Further, in certain installations, the meniscus insert may not require any attachment protrusion as the compression of the weight upon the ankle prosthesis 100 and the manner in which the installation is performed by the medical professional may allow the ankle prosthesis 100 assembly to hold the meniscus insert in place.

Additional embodiments include meniscus insert 130b having lips 139a extending forward and rearward of a concave recess 139 of meniscus insert 130b. Lips 139a are beneficial where sublexation, or anterior/posterior migration, of the ankle prosthesis 100 may occur. Thus, as the ankle joint may be thrust in a forward or rearward direction parallel to the surface of the ground once installed, lips 139a will assist the ankle prosthesis 100 from slipping out of position, which would potentially cause the ankle prosthesis 100 to become dislodged. However, it will be understood that lips 139a will further be shaped so as to prevent unwanted impingement of the user of the ankle prosthesis 100 while the ankle joint is undergoing plantar flexion and/or dorsiflexion.

As can be seen in FIG. 15, the talar component 120 generally forms a mound surface 129 having a generally convex shape. On the underside of the mound 129 is formed talar mounting portions 122 projecting away from a flat surface 124. Further, the mound surface 129, flat surface 124 and talar mounting portions 122 are intersected by sidewalls 125 of the talar component 120. Preferably, talar component 120 is provided with a wide base that approximates the shape of the talar section 46 of the talus 40 such that subsidence of the talar component 120 will be minimized.

Further, other embodiments may provide additional beneficial methods of preparation and talar components 120a, 120b to further prevent subsidence of the component wherein significant bone resection and implanting of the component will not cause the component to crush into the cancellous bone over time under pressure. As can be seen in FIGS. 18-21, differing talar sections 46a, 46b may be implemented in accordance with the present invention for use with talar components 120a,120b having surfaces 124a,124b, respectively. Likewise, matching cutting guides 90a,90b may be implemented to assist in the shaping of talar sections 46a,46b, respectively. More specifically, cutting slots 92a,92b having mount cut apertures 91 on cutting guides 90a,90b will assist in the shaping of the talar dome 42.

FIG. 17 illustrates ankle prosthesis 100 as it may be permanently positioned and prepared. As can be seen in FIGS. 14-17, the talar component 110 is attached to the meniscus insert 130 and rests on the talar component 120. More specifically, an upper surface 137 of the meniscus insert 130 interfaces with the recessed surface 117 as the meniscus insert 130 rotates within the inner walls 115. Further, the mound surface 129 of the talar component 120 interfaces with a concave recess 139 of the meniscus component 130. The interface between the talar component 120 and the meniscus insert 130 is further partially constrained to a rocking motion by the interface of recessed walls 135 of the meniscus insert 130 and the sidewalls 125 of the talar component 120. Accordingly, the interface between the tibial component 110 and the meniscus insert 130 permits the ankle prosthesis 100 limited rotational movement while the interface of the talar component 120 and the meniscus insert 130 provides limited front-to-back rocking motion for the patient receiving the ankle prosthesis 100.

The final steps in the method of preparation according to the present invention include replacing the medial portion 22 of the tibia 20 with at least one screw 29. Thus, the tibial chevron section 25 is resecured to the medial portion 22 of the tibia 20. The incision is then closed after the posterior tibial tendon retinaculum and superficial deltoid are repositioned or otherwise treated, thus completing the method for preparing the ankle for replacement according to the present invention.

Although the cutting alignment apparatus 50 may be employed at any time before the cutting step in the method of preparation described herein, it may be convenient to apply the cutting alignment apparatus 50 just before the cutting step implementing the cutting guide 90. However, other arrangements of the order of steps are contemplated to accomplish the method of preparation of the present invention. For example, it may be found convenient to apply the cutting alignment apparatus 50 to achieve greater confidence in alignment for certain medical professionals if implemented earlier in the process immediately before the cutting step implementing the cutting guide 90.

In addition, the present invention is applied from a medial approach that endures to the benefit of the medical professional in the ease of preparation of the ankle and the user of the ankle replacement for healing purposes and overall stability of the ankle joint after surgery. Further, because of the very common front to back rocking motion of the ankle (plantar flexion/dorsiflexion), the ability of the tibial and talar components to be mounted transversely, i.e., with mounting portions transverse to the motion/force applied to the ankle prosthesis, the ankle prosthesis is thus provided with immediate rigid fixation and further optimizes bony ingrowth of the ankle prosthesis.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A joint prosthesis, comprising:
a first joint component having a first locking feature and a recess;
a second joint component; and
a meniscus insert disposed between the first joint component and the second joint component and sized and shaped to be received within the recess of the first joint component, the meniscus insert having a second locking feature configured to engage the first locking feature such that the first joint component and the meniscus insert are prevented from disengaging one another while also permitting the meniscus insert to rotate with respect to the first locking feature within the recess of the first joint component wherein the joint prosthesis is structured to replace an ankle joint, the first joint component being configured to engage a tibia and the second joint component being configured to engage a talus.

2. The joint prosthesis of claim 1, wherein the first joint component is made of metal and the meniscus insert is made of polyethylene.

3. The joint prosthesis of claim 1, wherein the second locking feature includes a sphere-like element attached to a surface of the meniscus insert via a post; and
wherein the first locking feature is a corresponding recess that is engaged by the sphere-like element.

4. The joint prosthesis of claim 1, wherein the second locking feature is a circular ridge and the first locking feature is a number of corresponding grooves that are engaged by the circular ridge.

5. The joint prosthesis of claim 1, wherein the second locking feature includes a disk attached to a surface of the meniscus insert via a post and the first locking feature is a corresponding recess that is engaged by the disk.

6. The joint prosthesis of claim 1, wherein the meniscus insert includes a concave surface to interface with the second joint component.

7. The joint prosthesis of claim 6, wherein the meniscus insert includes lips extending from opposing sides of the concave surface to prevent the joint prosthesis from moving out of position.

8. The joint prosthesis of claim 1, wherein the second joint component includes a mound surface to interface with the meniscus insert.

9. The joint prosthesis of claim 1, wherein the first joint component includes a first mounting element configured to engage a first portion of bone.

10. The joint prosthesis of claim 1, wherein the second joint component includes a second mounting element configured to engage a second portion of bone.

* * * * *